(12) United States Patent
Doshi et al.

(10) Patent No.: US 9,796,981 B2
(45) Date of Patent: Oct. 24, 2017

(54) METHODS FOR TRANSFORMING TARWI AND FOR PRODUCING MOLECULAR FARMING PRODUCTS IN TRANSGENIC TARWI SEED

(71) Applicants: PRAIRIE PLANT SYSTEMS INC., Saskatoon (CA); NATIONAL RESEARCH COUNCIL OF CANADA, Ottawa (CA)

(72) Inventors: Ketan M. Doshi, Saskatoon (CA); Natalia N. Loukanina, Saskatoon (CA); Brent Pollock, Saskatoon (CA); Patricia Polowick, Saskatoon (CA); Larry Holbrook, Saskatoon (CA)

(73) Assignees: National Research Council of Canada, Ottawa (CA); PRAIRIE PLANT SYSTEMS INC., Saskatoon (CA)

( * ) Notice: Subject to any disclaimer, the term of this patent is extended or adjusted under 35 U.S.C. 154(b) by 1021 days.

(21) Appl. No.: 14/056,297

(22) Filed: Oct. 17, 2013

(65) Prior Publication Data
US 2014/0186924 A1    Jul. 3, 2014

Related U.S. Application Data

(60) Provisional application No. 61/715,995, filed on Oct. 19, 2012.

(51) Int. Cl.
  *C12N 15/82* (2006.01)
  *C12N 9/78* (2006.01)
(52) U.S. Cl.
  CPC ........... *C12N 15/8257* (2013.01); *C12N 9/78* (2013.01); *C12N 15/8205* (2013.01); *C12Y 305/04004* (2013.01)
(58) Field of Classification Search
  None
  See application file for complete search history.

(56) References Cited

PUBLICATIONS

Pigeaire et al (Molecular Breeding, 1997, 3: 34-349); cited on the IDS.*
Iantcheva et al. (Int. J. Dev. Biol., 2013, 57: 577-586).*
Babaoglu et al., (2000) Acta Physiologiae Plantarum, 22(2): 111-119.*
Asad et al., "Silicon carbide whisker-mediated embryogenic callus transformation of cotton (*Gossypium hirsutum* L.) and regeneration of salt tolerant plants", Mol. Biotechnol, Oct. 2008, vol. 40, pp. 161-169.
Ausubel et al., "Current Protocols in Molecular Biology", Unit 2.10, Hybridization Analysis of DNA Blots, John Wiley & Sons, New York, N.Y., 1993, 16 pages.
Babaoglu et al., "Agrobacterium-mediated transformation of *Lupinus mutabilis* L. using shoot apical explants", Acta Physiologiae Plantarum, 2000, vol. 22, No. 2, pp. 111-119.
Bean et al. "A simple system for pea transformation", Plant Cell Reports, May 1997, vol. 16, pp. 513-519.
Bottinger et al., "Agrobacterium-mediated transformation of Vicia faba", Molecular Breeding, Oct. 2001, vol. 8, pp. 243-254.
Chitty et al., "Genetic transformation in commercial Tasmanian cultivars of opium poppy, Papaver somniferum, and movement of transgenicpollen in the field", Functional Plant Biology, Oct. 20, 2003, vol. 30, pp. 1045-1058.
Daddona et al., "Human Adenosine Deaminase, cDNA and complete primary amino acid sequence", The Journal of Biological Chemistry, vol. 259, No. 19, Oct. 10, 1984, pp. 12101-12106.
Ellis et al., "Tissue-specific expression of a pea legumin gene in seeds of Nicotiana plumbaginifolia", Plant Molecular Biology, 1988, vol. 10, pp. 203-214.
Fischer et al., "Plant-based production of biopharmaceuticals", Current Opinion in Plant Biology, Apr. 7, 2004, vol. 7, pp. 152-158.
Gamborg et al., "Nutrient requirements of suspension cultures of soybean root cells", Experimental Cell Research, Apr. 1968, vol. 50, pp. 151-158.
Gelvin, "Agrobacterium-mediated plant transformation: the biology behind the "gene-jockeying" tool", Microbiology and Molecular Biology Reviews, Mar. 2003, vol. 67, No. 1, pp. 16-37.
Giusti et al., "Methods of Enzymatic Analysis", Section 3.4, Adenosine Deaminase, Colorimetric Method, 1984 vol. IV (pp. 315-323).
Hills, et al., "Genetic use restriction technologies [GURTs]: strategies to impede transgene movement", Trends in Plant Science, Mar. 13, 2007, vol. 12, No. 4, pp. 177-183.
Jaiswal et al., "Isolation of pigeon pea (*Cajanus cajan* L.,) legumin gene promoter and identification of conserved regulatory elements using tools of bioinformatics", Indian Journal of Biotechnology, Oct. 2007, vol. 6, pp. 495-503.
Jefferson, "Assaying chimeric genes in plants: The GUS gene fusion system", Plant Molecular Biology Reporter, Nov. 1987, vol. 5, No. 1, pp. 387-405.
Karimi et al., "Modular cloning in plant cells", TRENDS in Plant Science, Mar. 2005, vol. 10, No. 3, pp. 103-105.
Koncz et al., "The promoter of the TL-DNA gene 5 controls the tissue-specific expression of chimaeric genes carried by a novel type of Agrobacterium binary vector", Mol. Gen. Genet., Sep. 1986, vol. 204, pp. 383-396.

(Continued)

*Primary Examiner* — Cathy Kingdon Worley
*Assistant Examiner* — Stephen Uyeno
(74) *Attorney, Agent, or Firm* — Kathleen Marsman; Borden Ladner Gervais LLP

(57) ABSTRACT

The present disclosure describes reproducible methods for the *Agrobacterium*-mediated production of stable, genetically transformed, fertile tarwi plants (*Lupinus mutabilis* Sweet) having seed-specific expression of human adenosine deaminase enzyme (hADA) or a functional variant thereof. The method involves slicing a tarwi seed embryo to produce an explant; infecting the explant in co-cultivation medium containing an *agrobacterium* having a polynucleotide sequence encoding hADA or variant; thereby generating a transformed explant; elongating a transformed shoot from the transformed explant; and regenerating a transformed tarwi plant from the elongated shoot. Seeds and plants so formed are also described herein. Further, methods for the recovery and purification of recombinant hADA, or functional variant from a transformed tarwi plant are described.

16 Claims, 6 Drawing Sheets

(56) References Cited

PUBLICATIONS

Li et al., "Transgenic yellow lupin (*Lupinus luteus*)", Plant Cell Reports, May 2000, vol. 19, pp. 634-637.

Liu et al., "Signal Peptide of Potato PinII Enhances the Expression of Cry1Ac in Transgenic Tobacco", Acta Biochimica et Biophysica Sinica, 2004, vol. 36, No. 8, pp. 553-558.

Lycett et al., "The 5'-flanking regions of three pea legumin genes: comparison of the DNA sequences", Nucleic Acids Research, Sep. 25, 1985, vol. 13, No. 18, pp. 6733-6743.

Maliga, "Plastid transformation in higher plants", Annu. Rev. Plant Biol, Jan. 7, 2004, vol. 55, pp. 289-313.

Maniatis et al., "Molecular Cloning (A Laboratory Manual)", Cold Spring Harbor Laboratory, 1982, pp. 387-389.

Martinez-Navio et al., "An old enzyme for current needs: adenosine deaminase and a dendrytic cell vaccine for HIV", Immunology and Cell Biology, 2012, vol. 90, pp. 594-600.

Molvig et al., "Enhanced methionine levels and increased nutritive value of seeds of transgenic lupins (*Lupinus angustifolius* L.) expressing a sunflower seed albumin gene", Proc. Natl. Acad. Sci, USA, Agricultural Sciences, Aug. 1997, vol. 94, No. 16, pp. 8393-8398.

Mulin et al., "Organogenesis from hypocotyl thin cell layers of Lupinus mutabilis and Lupinus albus", Plant Growth Regulation, Feb. 2000, vol. 30, pp. 177-183.

Murashige et al., "A revised medium for rapid growth and bioassays with tobacco tissue cultures", Physiologia Plantarum, Jul. 1962, vol. 15, pp. 473-497.

Nadolska-Orczyk, "Somatic embryogenesis of agriculturally important lupin species, (*Lupinus angustifolius*, L. *albus*, L. *mutabilis*)", Plant Cell, Tissue and Organ Culture, Jan. 1992, vol. 28, pp. 19-25.

Nadolska-Orczyk et al., "Study of the factors influencing Agrobacterium-mediated transformation of pea (*Pisum sativum* L.)", Molecular Breeding, Apr. 2000, vol. 6, pp. 185-194.

Nguyen et al., "Agrobacterium-mediated transformation of sorghum (*Sorghum bicolor* (L.) *Moench*) using an improved in vitro regeneration system", Plant Cell Tissue Organ Cult, Nov. 2007, vol. 91, pp. 155-164.

Olhoft et al., "The role of thiol compounds in increasing Agrobacterium-mediated transformation of soybean cotyledonary-node cells",Plant Cell Rep, Dec. 2001, vol. 20, pp. 731-737.

Petolino et al., "Expression of murine adenosine deaminase (ADA) in transgenic maize", Transgenic Research, Feb. 2000, vol. 9, pp. 1-9.

Pigeaire et al., "Transformation of a grain legume (*Lupinus angustifolius* L.) via Agrobacterium tumefaciens-mediated gene transfer to shoot apices", Molecular Breeding, Oct. 1997, vol. 3, pp. 341-349.

Pniewski et al., "In vitro micropropagation of four lupin species", Acta Physiologiae Plantarum, 2002, vol. 24, No. 4, pp. 417-424.

Polowick et al., "Agrobacterium tumefaciens-mediated transformation of chickpea (*Cicer arietinum* L.): Gene integration, expression and inheritance", Genetics and Genomics, Plant Cell Rep, Dec. 2004, vol. 23, pp. 485-491.

Polowick et al., "The ability of pea transformation technology to transfer genes into peas adapted to western Canadian growing conditions", Plant Science, Apr. 25, 2000, vol. 153, pp. 161-170.

Rerie et al., "Nucleotide sequence of an A-type legumin gene from pea", Nucleic Acids Resesearch, Jan. 9, 1990, vol. 18, No. 3, pp. 655.

Schernthaner et al., "Control of seed germination in transgenic plants based on the segregation of a two-component genetic system", PNAS, May 27, 2003, vol. 100, No. 11, pp. 6855-6859.

Sharma et al., "Plants as bioreactors: recent developments and emerging opportunities", Biotechnology Advances, Nov.-Dec. 2009, vol. 27, pp. 811-832.

Singhabahu et al., "Production of human adenosine deaminase in tobacco BY2 calli and cell suspensions", Conference Proceedings from Molecular Pharming—recent progress in manufacturing medicines in plants, Sep. 21, 2012, 5 pages.

Spok et al., "Plant Molecular Farming; Opportunities and Challenges", JRC Scientific and Technical Reports, European Commission, 2008, EUR 23383, 148 pages.

Ward et al., "Protein purification", Current Analytical Chemistry, 2009, vol. 5, No. 2, pp. 1-21.

Ziolkowski, "Advancements in biolistics and applications for agriculturally significant crops", MMG 445 Basic Biotechnology eJournal, 2007, vol. 3, pp. 34-39.

Spok, "Molecular farming on the rise-GMO regulators still walking a tightrope", Trends in Biotechnology, Feb. 2007, vol. 25, No. 2, pp. 74-82.

Singhabahu et al., "Expression of a functional human adenosine deaminase in transgenic tobacco plants", Transgenic Research, Jun. 2013, vol. 22, pp. 643-649.

Krishnamurthy et al., "Agrobacterium mediated transformation of chickpea (*Cicer arietinum* L.) embryo axes", Plant Cell Reports, Jan. 2000, vol. 19, pp. 235-240.

Stacey et al., "Isolation of DNA from plants", Methods in Molecular Biology, Protocols for Nucleic Acid Analysis by Nonradioactive Probes, 1994, Human Press Inc., vol. 28, pp. 9-15.

Sambrook et al., "Molecular Cloning (A Laboratory Manual)", Cold Spring Harbor Laboratory, Cold Spring Harbor Laboratory Press, Third Edition, 2001, Cold Spring Harbor, NY, 6 pages.

Sawada et al., "PCR detection of Ti and Ri plasmids from phytopathogenic Agrobacterium strains", Applied and Environmental Microbiology, Feb. 1995, vol. 61, No. 2, 828-831.

Simpson et al., "Basic methods in protein purification and analysis: A laboratory manual", Cold Spring Harbor Laboratory Press, 2009, Cold Spring Harbor, NY, 59 pages.

\* cited by examiner 1   2   3   4   5   6

METHODS FOR TRANSFORMING TARWI AND FOR PRODUCING MOLECULAR FARMING PRODUCTS IN TRANSGENIC TARWI SEED

CROSS REFERENCE TO RELATED APPLICATIONS

This application claims the benefit of priority of U.S. Provisional Patent Application No. 61/715,995 filed Oct. 19, 2012, which is incorporated herein by reference in its entirety.

FIELD

The present disclosure relates generally to methods of transforming plants, seeds of transformed plants comprising proteins and methods of extracting proteins from seed. More particularly, the present disclosure relates to transgenic protein production in seeds of transformed tarwi (*Lupinus mutabilis* Sweet), and subsequent recovery and purification of transgenic proteins from said seed.

BACKGROUND

It is a primary goal of research efforts in plant biotechnology to genetically engineer plants so that they have a new or improved trait or characteristic. A specific example of great commercial interest is the production of commercially useful recombinant proteins in plants by a process known generally as plant molecular farming, (U.S. Pat. Nos. 4,956,282 and 5,550,036, Fischer et al., 2004, Spök et al., 2007).

Seeds are particularly useful as vehicles for the production of proteins for molecular farming applications as they are naturally developed for innate storing ability and stability. Examples of plants that have been engineered for seed specific expression and could be used for these purposes include corn, wheat, flax, sunflower, rice, soybean, canola, peanut, tobacco, *Arabidopsis* and castor, (U.S. Pat. Nos. 5,650,554, 5,693,506, and 7,157,629).

Examples of the types of transgenic molecular farming peptide or protein products that have been made in seed include enzymes, (U.S. Pat. Nos. 5,804,694, 6,087,558, 6,800,792, 5,994,628 and 7,390,936), enzyme inhibitors, (U.S. Pat. No. 5,824,870), structural proteins, (U.S. Pat. No. 6,617,431), hormones and growth factors, (U.S. Pat. Nos. 6,288,304 and 7,091,401), antibodies, (U.S. Pat. No. 6,417,429) and vaccine antigens, (U.S. Pat. Nos. 5,914,123, 5,654,184, and 6,761,914).

Although a wide range of different recombinant proteins have been made, and in some instances purified from seed, many of these processes have been undertaken using seeds of plants that constitute major food crops such as corn, rice, barley and canola. The use of major food crops for molecular farming purposes has caused regulatory and public acceptance concerns because of possible contamination of the food supply with unwanted recombinant products. The possibility of gene flow from these plants to wild relatives has also been cited as an environmental issue, (Hills, M., et al., 2007). Molecular methods to impede or block transgene movement have been developed, (Schernthaner, J. P., et al., 2003, U.S. Pat. Nos. 5,977,441, 5,723,765, 5,925,808, 7,452,986, 7,671,253, 8,124,843) but have not been widely used for a variety of reasons that are not related to the functionality of the technology.

Commonly used and easily transformed non-food species such as tobacco or *Arabidopsis* could be contemplated for molecular farming but these species have small seeds which makes larger scale production impractical. The large-seeded non-food crop Castor is problematic due to the severe toxicity of this species.

Tarwi, (*Lupinus mutabilis* Sweet) is a large-seeded legume that has been known and used since ancient times in South American Andean countries but is not grown in North America. It is adaptable, semi-hardy, nitrogen fixing and the mature plant, frost tolerant. Tarwi seeds contain an average of 46% protein, have a high lysine content, and contain 20% lipid, providing a nutritional balance equivalent to soybean. Some varieties have a high content of water soluble alkaloids that are easily removed by washing seed that has been soaked.

Large-seeded legumes are generally recalcitrant to transformation. A method of transforming beans is disclosed in WO 2012/0121494. However, it is known in the art that methods for transforming one type of legume typically do not translate well to other types of legumes. The type of tissue that is to be transformed and the various media combinations required are unpredictable and need to be developed specifically for individual species and even cultivars.

Tissue culture investigations of *L. mutabilis* have been limited but include: micropropagation (Pniewski et al. 2002), regeneration from thin-cell layers (Mulin and Bellio-Spataru, 2000) and somatic embryogenesis from immature cotyledons (Nadolska-Orczyk 1992). Genetic transformation has been reported for *Lupinus* species such as *L. angustifolius* L. (Pigeaire et al. 1997; Molvig et al. 1997) and *L. luteus* (Li et al. 2000).

There has been only one report of successful genetic transformation of *L. mutabilis* (Babaoglu et al. 2000). This study used shoot apical explants as the transformation target which is time consuming and impractical for large scale transformation studies (Babaoglu et al., 2000).

The process of expressing a desired gene in a plant involves constructing a vector that comprises the gene of interest downstream of a promoter, introducing the vector into a plant, and expressing the gene in the plant. In situations where stable expression of the gene is desired, the gene is incorporated into the genome. Generally, the foreign DNA is integrated into nuclear DNA, however methods for the integration of foreign DNA into the plastid genome have been developed for some plant species (U.S. Pat. Nos. 5,451,513; and 5,693,507).

It is desirable to be able to direct gene expression to a specific organ, such as a seed, in order to facilitate harvesting of proteins and to avoid protein production in other tissues which may have adverse effects on plant health or plant growth or could raise regulatory concerns. Researchers have identified a number of promoters that are useful for the expression of genes in seed. These include promoters related to storage gene products, seed components such as embryo, endosperm, ovule, seed coat etc., promoters active in early or late development and those that are specific to individual species. In legume seed described promoters include: a soybean lectin promoter; the conglycin promoter; the widely used 7S b-phaseolin storage protein promoter (U.S. Pat. No. 5,504,200); and the LegA2 *Pisum sativum* legumin gene promoter.

The LegA2 gene promoter from pea is described in Lycett Q. W., et al., (1985). This promoter was shown to function in tobacco, (Ellis et al., 1988). The legumin seed promoter has also been described from pigeon pea, (Jaiswal, R., et al., 2007), and more recently from non-leguminous species sorghum and maize (U.S. Pat. Nos. 7,897,841, 7,622,637 and 7,211,712).

Many different procedures have been described that physically introduce foreign DNA into plant cells. A common strategy has been the "biolistic" acceleration of small dense carrier particles, such as particles of gold that are coated in foreign DNA, by what is known in the art as a "gene gun" (U.S. Pat. No. 4,945,050; 5,036,006; and 5,371, 015). A variety of different "gene guns" for shooting DNA into plant cells have been developed (Ziolkowski, 2007; U.S. Pat. Nos. 5,976,880; 5,584,807). Other physically carriers such as tungsten "whiskers" or silicon carbide crystals have also been used to deliver foreign DNA by puncture of the cell wall creating channels for DNA entry (Asad, S., et al. 2008; U.S. Pat. Nos. 5,302,523, 5,464,765; 7,259,016: 6,350,611).

Other physical approaches have included the micro-injection of DNA solutions directly into cell nuclei, (U.S. Pat. Nos. 4,743,548, 5,994,624) and production of pores in cellular membranes for DNA uptake with electric currents (U.S. Pat. No. 6,022,316). The removal of the external cell wall barrier and preparation of protoplasts facilitates the uptake of DNA directly from solution but in some instances regeneration of plants from protoplasts is challenging (U.S. Pat. Nos. 4,684,611; and 5,453,367).

By far the most widely practiced general method of achieving plant transformation has been by the use of disarmed strains of *Agrobacteria* (as reviewed in Gelvin, 2003). *Agrobacterium tumefaciens* and related soil bacteria naturally comprise a DNA plasmid (i.e. a T-DNA plasmid) that is physically mobilized into plant cells by bacteria proliferating in a wound site. The T-DNA plasmid has left and right border sequences that are required for integration of DNA into the plant host genome. Foreign DNA between the border sequences is thus selectively introduced into the host genome.

Naturally occurring *Agrobacterium* species introduce foreign DNA that comprises genes for the production of plant growth regulatory substances and uncommon amino acid metabolites known as opines. This results in the formation of a tumour at the site of infection that in addition to providing a refuge for the growth of *Agrobacteria* supplies specific nutrients beneficial to the bacteria. The formation of crown gall tumours, (or hairy root proliferation) by *Agrobacterium* sp. is an example of molecular parasitism. Naturally occurring plasmids have been modified, "disarmed" by removal of genes that cause tumor formation and support bacterial growth. The Ti plasmid was also modified to remove so-called virulence factors needed for DNA transfer. These factors were placed on a separate plasmid so that only selective recombinant DNA is added to the host plant cells and not the Vir genes. The technique of removal of the virulence factor DNA to a separate plasmid is known as "disarming" and resulted in the development of the preferred binary transformation method (U.S. Pat. No. 4,940,838).

Initially, it was felt that *Agrobacterium* mediated transformation only occurred with dicot species however over time *Agrobacterium* strains that infect monocots were discovered and transformation using *Agrobacterium* was demonstrated (U.S. Pat. Nos. 5,591,616; and 7,060,876).

An important consideration for regeneration of transformed plants is the tissue targeted for biolistic or *Agrobacterium* mediated transformation. Tissue targets that have been shown to be useful for the regeneration of transformed plants include: leaf discs, stem segments, petioles, decapitated meristems, roots, flower buds and pollen. Any tissue can be used that can subsequently be regenerated into whole functional transgenic plants.

An example of a therapeutically useful enzyme is adenosine deaminase (E. C. 3.5.4.4). In humans, adenosine deaminase is needed for the breakdown of adenosine from food and the turnover of nucleic acids in tissues. A primary function of this enzyme is in the development and maintenance of the immune system. The ADA active site contains a zinc atom, the only cofactor needed for enzymatic activity.

Mutations in the adenosine deaminase gene result in reduced or a complete lack of expression resulting in a disease condition known as Severe Combined Immune Deficiency, (SCID). SCID is considered an orphan disease, occurring with a frequency of less than one in 100,000 live births worldwide. ADA is needed to break down metabolic byproducts that become toxic to T-cell lymphocytes. Most other cells have alternate means of removing these byproducts and are less affected by ADA deficiency. T-cells of SCID individuals die a few days after being produced in contrast to a normal life span of a few months. Consequently, T-cell numbers are greatly depleted. Because T-cells control B-cell activity, the reduction in T-cells results in the absence of both T-cell and B-cell function resulting in severe combined immune deficiency. SCID victims are unable to mount an effective immune response to any infections, a defect that is soon fatal.

Several clinical approaches for SCID have been explored including bone marrow transplants and gene replacement therapy, however the most widely used approach is via enzyme replacement therapy. Patients receive weekly or twice weekly injections of the ADA enzyme which is typically presented in a PEGylated form to slow degradation. The ADA used for replacement therapy is derived from bovine sources. Currently, the cost to supply SCID patients with bovine ADA is in excess of 100,000 dollars per annum per patient. ADA may have additional therapeutic uses in treatment of other immune disorders, (U.S. Pat. No. 5,728, 560), HIV (Martinez-Navio et al., 2011) and cancer, (U.S. Patent application 20090047270).

The human form of the enzyme is inherently less stable than the bovine enzyme due to a reactive unpaired cysteine on the enzyme surface. The bovine enzyme has the same number of primary cysteine residues in the same locations as the human enzyme but the reactive cysteine is post-transcriptionally capped with an additional cysteine residue. The primary amino acid sequence of human ADA has been known for some time (Daddona et al., 1984) which has allowed researchers to design modifications and amino acid substitutions to reduce instability (U.S. Pat. No. 8,071,741).

Although it is now known how to increase the stability of recombinant ADA, the human enzyme is largely available in a crude form made in *E. coli*. Filpula et al, (U.S. Pat. No. 8,071,741) exemplify the substitution in hADA of the reactive cysteine with serine but only contemplate recombinant production in bacteria and yeast.

Transient transformation of tobacco BY-2 cells with hADA genes for the purpose of producing biologically active hADA has been proposed (Singhabahu et al., 2010; Singhabahu and Bringloe 2012). It appears that the researchers were able to isolate ADA from cell cultures of transgenic tobacco cells and transgenic calli, but it was not demonstrated that the isolated protein is active or stable. The use of transient systems for molecular farming has the disadvantage that a desired product must be harvested or isolated immediately.

Thus there remains a need for methods of safely producing large amounts of therapeutically useful enzymes, such as hADA. In addition, there remains a need for efficient and reproducible methods for transforming *Lupinus mutabilis*.

SUMMARY

Generally, the present disclosure provides methods of producing transformed tarwi (*Lupinus mutabilis* Sweet) comprising human adenosine deaminase (hADA) or a functional variant thereof, tarwi seeds comprising hADA and methods of recovering and purifying hADA or a functional variant thereof, from tarwi seeds.

There is described herein a method of producing transformed tarwi comprising a human adenosine deaminase (hADA) or a functional variant thereof. The method includes: slicing at least one tarwi seed embryo to produce at least one explant; infecting the explant by incubating the explant in a co-cultivation medium comprising *agrobacterium*, wherein the *agrobacterium* comprise a polynucleotide sequence encoding human adenosine deaminase (hADA) or functional variant thereof; thereby generating a transformed explant; elongating at least one transformed shoot from the transformed explant to form an elongated shoot; and regenerating a transformed tarwi plant from the elongated shoot.

A transformed plant, a transformed seed, a transformed cell and a tarwi seed comprising a human adenosine deaminase or functional variant thereof are also described.

There is also described herein a method of purifying human adenosine deaminase (hADA) or functional variant thereof from a tarwi seed. The method includes: a) extracting protein from the seed; b) passing the extracted protein through a dye affinity column to collect the dye affinity column flowthrough; c) salting the dye affinity column flowthrough to produce a salted dye affinity column flowthrough; d) filtering the salted dye affinity column flowthrough and collecting the filtrate; e) passing the filtrate through a hydrophobic interaction chromatography column to bind the hADA or functional variant thereof; f) eluting the hADA or functional variant thereof from the hydrophobic interaction chromatography column; g) desalting the eluted hADA to produce a desalted eluate; h) passing the desalted eluate through an anion exchange chromatography column to bind the hADA or functional variant thereof; and i) eluting the hADA or functional variant thereof from the anion exchange chromatography column to generate purified hADA or functional variant thereof.

Without limiting the invention to any particular theory of operation or benefit, the methods described above provide an improved platform for molecular farming of human adenosine deaminase.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached figures, described below.

DETAILED DESCRIPTION

Figure 1:
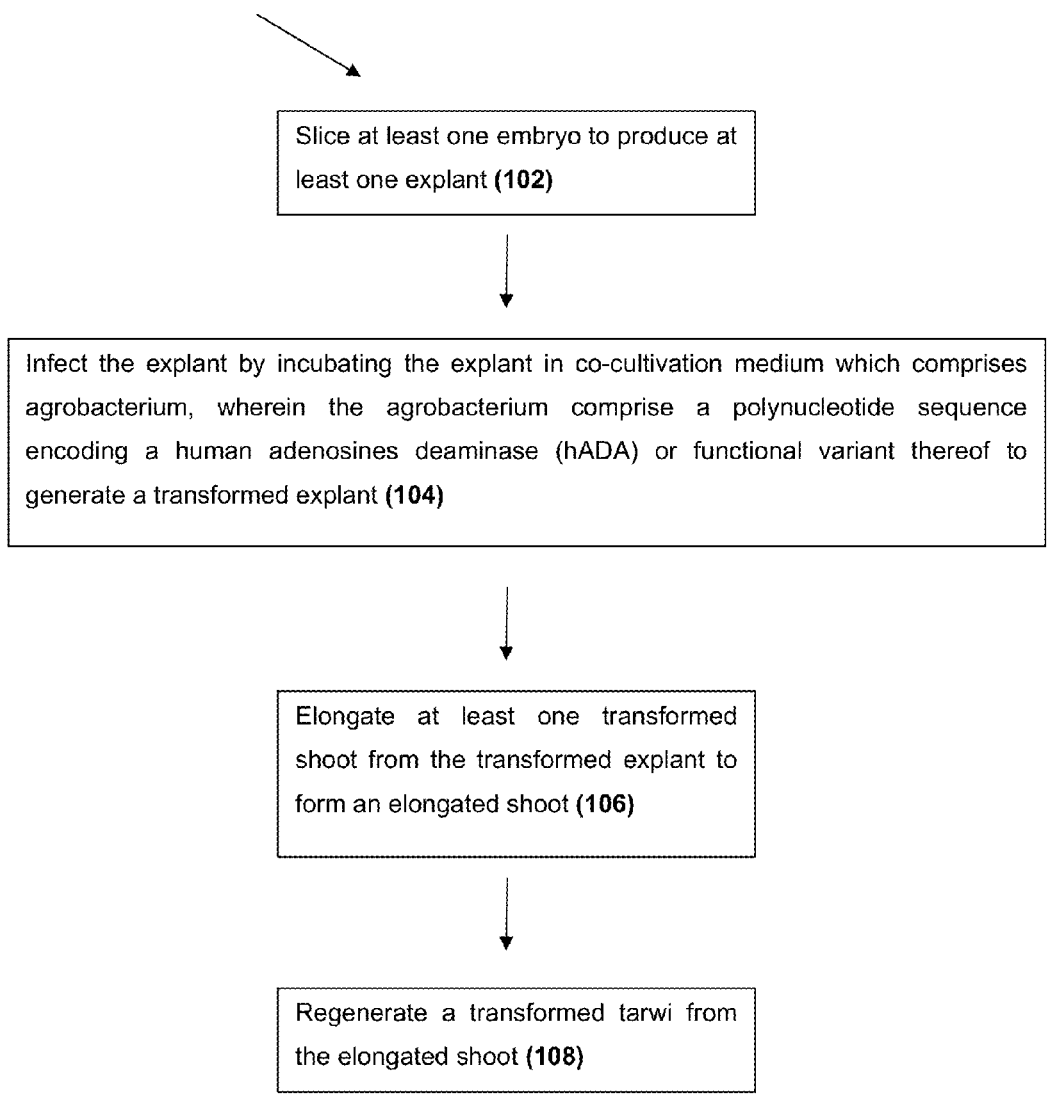
FIG. 1 is a schematic illustrating a method of producing transformed tarwi comprising a human adenosine deaminase (hADA) or a functional variant thereof.

Generally, the present disclosure provides a method of transforming tarwi, tarwi cells expressing human adenosine deaminase (hADA) and a method of purifying ADA from tarwi seed.

SEQ ID NO:1 refers to the amino acid sequence of a human ADA protein.

SEQ ID NO:2 refers to the amino acid sequence of a human ADA protein with cysteine at position 75 mutated to serine to increase stability.

SEQ ID NO:3 refers to the cDNA sequence of a human ADA.

SEQ ID NO:4 refers to the cDNA sequence of a human ADA that has been back translated to utilize the codon preferences of pea.

SEQ ID NO:5 refers to the cDNA sequence of a human ADA that has been back translated and encodes a cysteine at position 75

SEQ ID NO:6 refers to the LegB4Fw primer.
SEQ ID NO:7 refers to the LegB1Ry primer.
SEQ ID NO:8 refers to the PinllB1Fw primer.
SEQ ID NO:9 refers to the PinllB2Ry primer.
SEQ ID NO:10 refers to the hADAB2Fw primer.
SEQ ID NO:11 refers to the hADAB3Rv primer. SEQ ID NO:12 refers to the hADA-fw primer. SEQ ID NO:13 refers to the hADA-rv primer.

There is described herein a method of producing transformed tarwi comprising a human adenosine deaminase (hADA) or a functional variant thereof. A tarwi seed embryo is sliced to produce at least one explant. The explant is infected by incubating the explant in co-cultivation medium which comprises *agrobacterium*, wherein the *agrobacterium* comprise a polynucleotide sequence encoding a human adenosine deaminase (hADA) or functional variant thereof; thereby generating a transformed explant. A transformed shoot is elongated from the transformed explant to form an elongated shoot. A transformed tarwi plant is regenerated from the elongated shoot.

The method may comprise slicing the tarwi seed embryo longitudinally using a scalpel having the agrobacterium thereon. The co-cultivation medium may comprise Gamborg B5 salts and may be essentially free of auxins or cytokinins. The explants and transformed explants may be cultured in ventilated MAGENTA™ jars. The elongated shoot may be removed from the explant prior to regeneration. The method may include inducing root formation from the elongated shoot by incubating the shoot in a rooting medium comprising Indole-3-butyric acid (IBA), to root the elongated shoot.

The hADA may comprise the amino acid sequence of SEQ ID NO:1 and the functional variant of hADA may comprise an amino acid sequence that is at least 80% identical to the amino acid sequence of SEQ ID NO:1 and is capable of deaminating adenosine. The functional variant of hADA may comprise the sequence as set forth in SEQ ID NO:2.

The polynucleotide sequence may be set forth in SEQ ID NO:3, SEQ ID NO:4 or SEQ ID NO:5; or may be a polynucleotide sequence with 80% or greater identity to SEQ ID NO:3, SEQ ID NO:4 or SEQ ID NO:5 which hybridizes to the complement of SEQ ID NO:3, SEQ ID NO:4 or SEQ ID NO:5 under stringent conditions.

The polynucleotide sequence may have at least 85%, at least 90% or at least 95% identity to SEQ ID NO:3, SEQ ID NO:4 or SEQ ID NO:5.

In another aspect, there is described herein a transformed plant produced by the method described above or a transformed seed of the plant. A transformed cell of the seed described herein is also provided.

There is also described herein a tarwi seed comprising: a human adenosine deaminase (hADA) or variant thereof wherein the variant is capable of deaminating adenosine, and a cell of the tarwi seed.

There is further described a method of purifying human adenosine deaminase (hADA) or functional variant thereof from a tarwi seed. The method includes: a) extracting protein from the seed; b) passing the extracted protein through a dye affinity column to collect the dye affinity column flowthrough; c) salting the dye affinity column flowthrough to produce a salted dye affinity column flowthrough; d) filtering the salted dye affinity column flowthrough and collecting the filtrate; e) passing the filtrate through a hydrophobic interaction chromatography column to bind the hADA or functional variant thereof; f) eluting the hADA or functional variant thereof from the hydrophobic interaction chromatography column; g) desalting the eluted hADA to produce a desalted eluate; h) passing the desalted eluate through an anion exchange chromatography column to bind the hADA or functional variant thereof; and i) eluting the hADA or functional variant thereof from the anion exchange chromatography column to generate purified hADA or functional variant thereof.

The transformed tarwi may be from known and characterized cultivars of Lupinus mutabilis and naturally occurring feral forms of Lupinus mutabilis.

As used herein, the term "adenosine deaminase" (ADA) refers to an enzyme that is capable of adenosine deaminase activity. ADA may be in the form of a monomer or dimer complex. The term "human adenosine deaminase (hADA)" refers to a protein or polypeptide of native human adenosine deaminase, for example proteins purified from a human source. hADA may comprise the amino acid sequence set forth in SEQ ID NO:1.

The cells may also comprise "functional variants" of hADA that have a function that is substantially similar to hADA. A "functional variant" includes an ADA protein or polypeptide comprising an amino acid sequence that is at least 80% identical to the amino acid sequence of a human adenosine deaminase along the entire length of the protein. A variant may contain amino acid substitutions, insertions, deletions, post translational modifications or other modifications. Amino acid-substituted variants of hADA may include stabilized versions of hADA. Stabilized ADA may have oxidizable amino acids residues replaced with non-oxidizable amino acid residues; examples of which can be found in U.S. Pat. No. 8,071,741. An ADA variant may include the protein set forth in SEQ ID NO:2. An ADA variant may also comprise naturally occurring variants for example those found in the protein sequence database "Uniprot" maintained by the European Bioinformatics Institute (EBI), the Swiss Institute of Bioinformatics (SIB) and the Protein Information Resource (PIR), under, for example, accession number P00813. An ADA variant may be an isoform of ADA. Fragments having at least 80% identity to the sequence of hADA are considered to be functional variants as described herein, provided such variants maintain a function that is substantially similar to hADA. For example, a fragment that comprises 80% (or more) of hADA, but not the entire length of hADA are encompassed herein.

A functional variant of ADA may also include a fragment of ADA that retains the ability to deaminate adenosine.

The "ability to deaminate adenosine" is defined as the ability to catalyze the deamination reaction of adenosine to inosine at a level equivalent to at least 80% of that of wild type ADA. This reaction is based on the enzymatic deamination of adenosine to inosine which is converted to hypoxanthine by purine nucleoside phosphorylase (PNP). Hypoxanthine is then converted to uric acid and hydrogen peroxide ($H_2O_2$) by xanthine oxidase (XOD). $H_2O_2$ is further reacted with N-Ethyl-N-(2-hydroxy-3-sulfopropyl)-3-methylaniline (EHSPT) and 4-aminoantipyrine (4-AA) in the presence of peroxidase (POD) to generate quinone dye which is monitored in a kinetic manner at 550 nm.

An adenosine deaminase assay is described in Petolino et al., which is a modification of an assay described by Gusti and Galanti (1984), that measures ammonia formation when adenosine is used as substrate. Commercial assays are available from, for example, Bio-Quant (San Diego, Calif.).

A "polynucleotide sequence encoding a human adenosine deaminase" refers to a nucleic acid molecule that encodes a human adenosine deaminase protein, polypeptide or fragment or variant thereof. Thus, such a sequence is often a cDNA sequence that encodes human adenosine deaminase, for example Genbank Accession number X02994.1. In other embodiments, a sequence encoding a human adenosine deaminase may include sequences, such as introns that are not present in a cDNA. In other embodiments a polynucleotide sequence encoding a human adenosine deaminase may comprise an artificial sequence that is back translated from a human deaminase protein sequence to alter the codon preference to that of a legume, such as pea, in order to increase the translation of hADA in tarwi. Examples of such sequences are set forth in SEQ ID NO: 4 and SEQ ID NO:5.

A "polynucleotide sequence" unless otherwise limited encompasses known analogues of natural nucleotides that hybridize to nucleic acids in a manner similar to naturally occurring nucleotides.

"Identity" is used interchangeable with "percentage sequence identity" or "percentage (%) identity" and is determined by comparing two optimally aligned sequences over a comparison window, wherein the portion of the nucleic acid or amino acid sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Percentage identity can be any integer from 80% to 100%. Exemplary embodiments include at least: 80%, 81%, 82%, 83%, 84%, 85%, 86%, 87%, 88%, 89%, 90%, 91%, 92%, 93%, 94%, 95%, 96%, 97%, 98% or 99% or more identity compared to a reference sequence using the programs described herein; preferably BLAST using standard parameters.

The person skilled in the art will understand that optimal alignment of sequences for comparison may be conducted by the local homology algorithm, by the homology alignment algorithm, by the search for similarity method, by computerized implementations of these algorithms (GAP, BESTFIT, BLAST, FASTA, TFASTA, and DASH), or by inspection.

As used herein "stringent hybridization conditions" or "stringent conditions" refers to conditions under which a probe will hybridize to its target subsequence, typically in a complex mixture of nucleic acid molecules, with little or no binding to other sequences. Stringent conditions are sequence-dependent and will be different in different circumstances. Longer sequences hybridize specifically at higher temperatures. Generally, stringent conditions are selected to be about 5-10° C. lower than the thermal melting point (Tm) for the specific sequence at a defined ionic strength pH. The Tm is the temperature (under defined ionic strength, pH, and nucleic acid molecule concentration) at which 50% of the probes complementary to the target hybridize to the target sequence at equilibrium (as the target sequences are present in excess, at Tm, 50% of the probes are occupied at equilibrium). Stringent hybridization conditions will be those in which the salt concentration is less than about 1.0 M sodium ion, typically about 0.01 M to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent hybridization conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 55° C., 60° C., or 65° C. Such washes can be performed for 5, 15, 30, 60, 120, or more minutes.

In some embodiments "stringent conditions" are, for example, conditions that allow hybridization comparable with the hybridization that occurs using a DNA probe that may be 500 nucleotides in length, in a buffer containing 0.5 M $Na_2HPO_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. (These are typical conditions for high stringency northern or Southern hybridizations). Those of ordinary skill in the art will readily recognize that alternative hybridization and wash conditions can be utilized to provide conditions of similar stringency, such as those described in Maniatis et al. in Molecular Cloning: A Laboratory Manual, Cold Spring Harbor Laboratory, (1982) p. 387 to 389. Hybridizations may be carried out over a period of about 20 to 30 minutes, or about 2 to 6 hours, or about 10 to 15 hours, or over 24 hours or more. High stringency hybridization is also relied upon for the success of numerous techniques routinely performed by molecular biologists, such as high stringency PCR, DNA sequencing, single strand conformational polymorphism analysis, and in situ hybridization. In contrast to northern and Southern hybridizations, these techniques are usually performed with relatively short probes (e.g., usually about 16 nucleotides or longer for PCR or sequencing and about 40 nucleotides or longer for in situ hybridization). The high stringency conditions used in these techniques are well known to those skilled in the art of molecular biology, and examples of them can be found, for example, in Ausubel et al., Current Protocols in Molecular Biology, John Wiley & Sons, New York, N.Y., 1998, and in Maniatis et al., in Molecular Cloning: A Laboratory Manual, Cold Spring Harbor Laboratory, (1982). A nucleic acid sequence may be detectably labeled.

As used herein the term "encodes" refers to a nucleic acid or polynucleotide which comprises the information for translation into the specified protein.

The term "dye affinity column" refers to a column that comprises immobilized dyes of high affinities for the binding sites on proteins. For example, an Affi-Gel Blue Gel column can be used. Cibacron® Blue F3GA dye used in this medium.

The term "hydrophobic interaction column" is meant to include any chromatography column with medium to high hydrophobicity. Hydrophobic interaction columns can be used in the capture of intermediate stages of protein purification. Such columns bind hydrophobic areas on a protein(s) to the hydrophobic area of the column. Generally, proteins bind a hydrophobic interaction column at a high salt concentration and elute at a low salt concentration.

As used herein the term "anion exchange column" includes any anion exchange column that comprises a positively charged support which separates proteins of negative charge.

As used herein the term "salting" is used interchangeably with antisolvent crystallization, precipitation, or precipitation crystallization and refers to a method of separating proteins based on the principle that proteins are less soluble at high salt concentrations. The salt concentration needed for the protein to precipitate out of the solution differs from protein to protein. The salt is a salt that is not detrimental to the protein and may be, for example ammonium sulfate.

The construction of vectors suitable for transformation of plants is known and routine to a person of skill in the art. The vector includes a promoter that may be organ specific (i.e. that may direct expression to a specific organ). The promoter is operatively linked to a polynucleotide sequence that encodes a human adenosine deaminase. The vector may include enhancers, either translational or transcriptional enhancers as may be required.

The vector may further comprise a selectable marker gene. Selectable marker genes are well known in the art and include enzymes that provide antibiotic (i.e. kanamycin, hygromycin, spectinomycin) resistance or a visual colour change of cells and tissues and includes all genes that can help differentiate transformed and non-transformed cells. Examples of visual markers include the microbial beta-glucuronidase gene, (GUS) and the green fluorescent protein, (GFP) without being limited thereto.

The present disclosure discloses a method for producing tarwi (*Lupinus mutabilis* Sweet) expressing recombinant human adenosine deaminase. A schematic of a method of producing transforming tarwi is outlined in FIG. 1. The method of producing transformed tarwi or functional variant thereof (100) includes slicing at least one embryo to produce at least one explant (102). The explant is infected by incubating the explant in co-cultivation medium which comprises *agrobacterium*, wherein the *agrobacterium* comprise a polynucleotide sequence encoding a human adenosine deaminase (hADA) or functional variant thereof to generate a transformed explant (104). An elongated shoot is elongated from the transformed explant (106). A transformed tarwi is regenerated from the elongated shoot (108).

Figure 2:
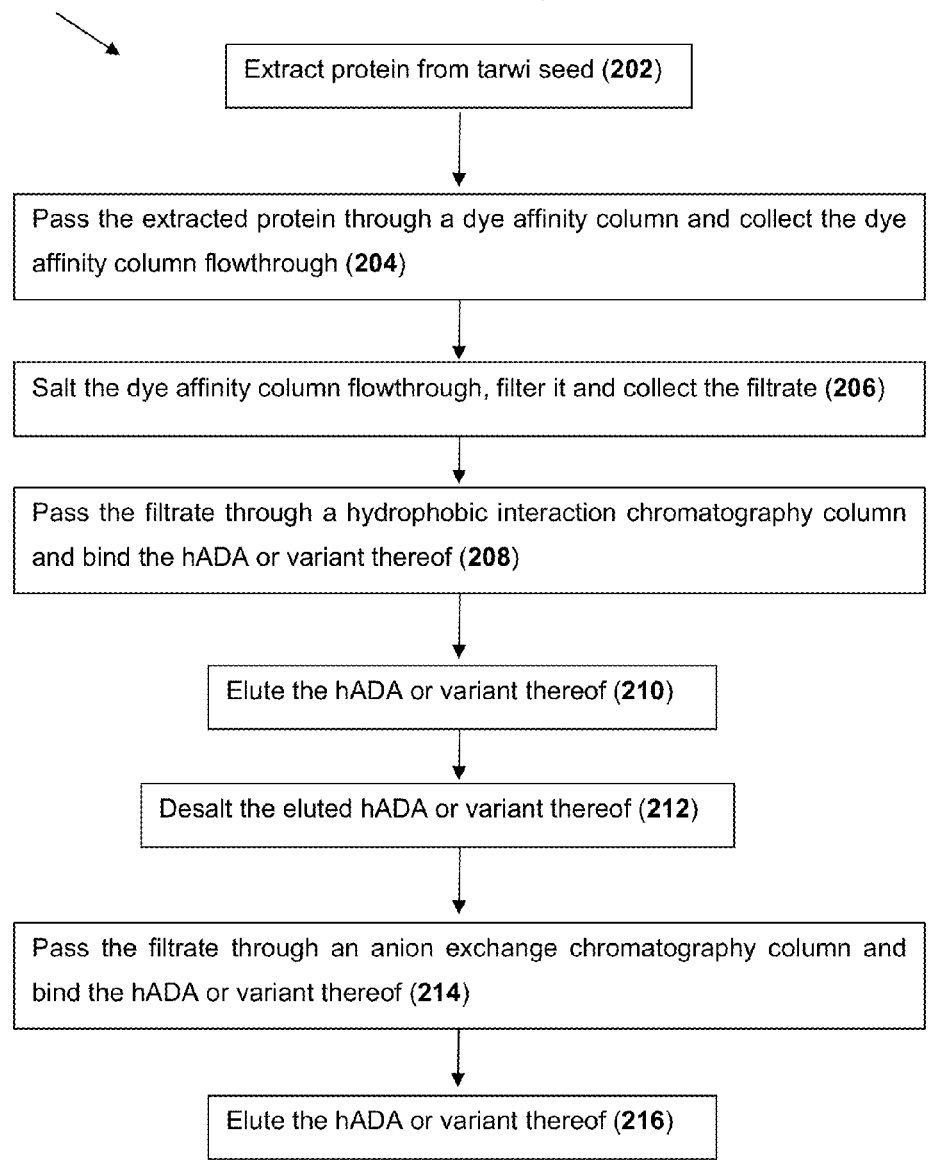
FIG. 2 is a schematic illustrating a method of purifying adenosine deaminase (hADA) or functional variant thereof from a tarwi seed.

A schematic of a method of purifying hADA or functional variant thereof from a tarwi seed is shown in FIG. 2. The method of purifying hADA or functional variant thereof from a tarwi seed (200) includes extracting protein from at least one tarwi seed (202). The extracted protein is passed through a dye affinity column and the dye affinity column flowthrough is collected (204). The dye affinity flowthrough is salted and filtered and the filtrate is collected (206). The collected filtrate is passed through a hydrophobic interaction chromatography column and the hADA or functional variant thereof is bound to the column (208). The bound hADA or functional variant thereof is eluted (210). The eluted hADA or variant thereof is desalted (212). The eluted hADA or variant thereof is passed through an anion exchange column and the hADA or functional variant thereof is bound to the column (214). The bound hADA or functional variant thereof is eluted (216).

The following examples are provided to illustrate the transformation method and production and purification of recombinant proteins of the present invention and should not be interpreted in any way to limit the scope of the invention.

EXAMPLE 1

Construction of a PPS2 hADA Transformation Vector

The PPS2 expression vector was constructed to express the human adenosine deaminase enzyme in tarwi seed The PPS2 vector contains the LegA2 seed specific promoter from pea (Rerie et al. 1991) a potato proteinases inhibitor II (PinII) apoplast-specific targeting sequence, (Gene Bank Accession #X04118), (Liu et al. 2004) and a CaMV 35S terminator. The amino acid sequences of a hADA (GenBank: CAH73885.1) was back-translated using the codon preference of legumes, and the resulting artificial ORF was synthesized at the NRC-PBI, DNA sequencing facility.

Three DNA fragments (attB4-LegA2-attB1, attB1-PinII-attB2 and attB2-hADA-attB3) were amplified by polymerase chain reaction (PCR) using specific pairs of primers and template DNA (Table 1). The sequence of these fragments was verified by automated nucleotide sequencing at NRC-PBI (National Research Council of Canada-Plant Biotechnology Institute, Saskatoon).

Table 1 lists primers and template DNA used for generating entry clones.

TABLE 1

List of primers and template DNA used for generating entry clones

| Amplified DNA fragments with specific recombines site | Pair of primers | Template DNA (Plasmid pBluskript II KS(+) carries following DNA sequence) | Source |
|---|---|---|---|
| attB4-LegA2-attB1 (Size 857 bp) | LegB4Fw 5'GGGGACAACTTTGTATAGAAAAGTTGAA TTCCTTCTTAATGGTAGTCTAGTTTA 3' (SEQ ID NO: 6) LegB1Rv 5'GGGGACTGCTTTTTTGTACAAACTTGTG GTTGGATAGAATATATGTTTGTGAC 3' (SEQ ID NO: 7) | LegA2 Pea seed specific promoter (Gene Bank Accession # X17193) | Dr. Patricia Polowick, (NRC-PBI) |
| attB1-PinII-attB2 (size 279 bp) | PinIIB1Fw 5'GGGGACAAGTTTGTACAAAAAAGCAGGC TATTCACAGACACTCTTCACCCCAA 3' (SEQ ID NO: 8) PinIIB2Rv 5'GGGGACCACTTTGTACAAGAAAGCTGGG TAAGCCTTCGCATCAACATGCTCCAT 3' (SEQ ID NO: 9) | PinII (Potato Proteinase inhibitor II) apoplast specific signal peptide (Gene Bank Accession # X04118) | A 279 bp PinII DNA sequence was synthesized at NRC-PBI, DNA sequencing facility |
| attB2-hADA-attB3 (size 1092 bp) | hADAB2Fw 5'GGGGACAGCTTTCTTGTACAAAGTGGTG CCTAGAATGGCTCAAACTCCTGCTTTTGA T 3' (SEQ ID NO: 10) hADAB3Rv 5' GGGGACCACTTTGTACAAGAAAGCTGG GTTTATTAAAGATTTTGACCAGCAGA 3' (SEQ ID NO: 11) | ORF of hADA gene (human Adenosine Deaminase gene) | A 1092 bp artifical ORF was synthesized at NRC-PBI, DNA sequencing facility |

The entry clones were obtained by BP clonase reaction between said three DNA fragments and specific donor clones from Gateway (Invitrogen; Catalogue #12537-023). The vector pER598 was derived from pKm43GW (Karimi et al. 2005) used as a destination clone. A binary vector pLPhA was generated by inserting a single gene cassette into pER598 using LR clonase reactions to transfer the gene cassette from the entry clone to the destination vector were performed according to the protocol of the MultiSite Gateway Three Fragment Vector Construction Kit (Invitrogen; Catalogue #12537-023). The vector was electroporated into disarmed *Agrobacterium tumefaciens* strain GV3101-pMP90 (Koncz and Schell, 1986) prior to plant transformation experiments.

Media Composition

A range of media were evaluated for plant tissue co-cultivation of tarwi tissues with *Agrobacteria* that ranged from a few simple salts to complete basal media, both with and without plant growth regulators and acetosyringone. Different explants, including whole seed, cotyledons and entire but wounded embryo axes were tested. The media and methods that resulted in the successful generation of transgenic plants are described and the components of the relevant media are listed in Table 2. Except where stated otherwise, all media contained 3% sucrose, were adjusted to a pH of 5.7, solidified with agar and sterilized by autoclaving. All media, except for the co-cultivation medium, contained the antibiotic mixture of Timentin (200 mg l-1; GlaxoSmithKline, Research Triangle Park, N.C., US) to check the growth of residual *Agrobacterium* and kanamycin to kill untransformed tissue. Acetosyringone, kanamycin and Timentin were filter-sterilized prior to incorporation into the culture media.

The co-cultivation medium was comprised of B5 salts and vitamins and supplemented with acetosyringone (200 μM). The shoot-inducing medium also contained Gamborg's (Gamborg et al. 1968) B5 salts and vitamins supplemented with benzylaminopurine (BAP 13 μM) and kanamycin at 50 mg/L. In the shoot elongation medium, B5 salts were substituted with MS salts (Murashige and Skoog 1962), the BAP concentration was reduced to 0.5 μM and the kanamycin concentration was halved to 25 mg/L. The rooting medium consisted of Gamborg's B5 salts and vitamins, 2% sucrose and 20 μM indole butyric acid (IBA). The concentration of antibiotics in the rooting medium was retained as in the shoot elongation medium (Table 2).

Co-cultivation

Longitudinal slices through mature embryo axes of an imbibed seed, or inoculated explants, were placed onto sterile filter paper on the surface of the co-cultivation medium (302), which consisted of Gamborg's B5 medium with acetosyringone but without added plant growth regulators (Table 2). The addition of plant growth regulators (auxins and/or cytokinins) limited both the regeneration of the tarwi explants and transient expression of reporter genes. Plates with explants were incubated for 4 days in the dark at room temperature (23° C.).

Shoot Induction

After 4 days of co-cultivation, explants were transferred to shoot inducing medium (304), as outlined in Table 2). The inclusion of filter paper on the surface of the co-cultivation medium obviated the requirement to rinse explants in

TABLE 2

Media Composition

| Components[a] | Co-cultivation medium | Shoot induction medium | Shoot elongation medium | Rooting medium |
|---|---|---|---|---|
| Macro- and micro-salts | Gamborg B5[b] | Gamborg B5 | MS[c] | Gamborg B5 |
| Vitamins | Gamborg B5[d] | Gamborg B5 | Gamborg B5 | Gamborg B5 |
| 6-Benzylaminopurine (BAP) | — | 13 μM | 0.5 μM | — |
| Indole-3-butyric acid (IBA) | — | — | — | 20 μM |
| Sucrose | 30,000 | 30,000 | 30,000 | 30,000 |
| Acetosyringone | 200 μM | — | — | — |
| Kanamycin | — | 50 | 25 | 25 |
| Timentin | — | 200 | 200 | 200 |
| Agar | 7,000 | 7,500 | 7,000 | 8,000 |
| pH | 5.75 | 5.75 | 5.75 | 5.6 |

[a]Except where stated, concentrations for components are mg/L
[b]B-5 basal salt mixture as described by Gamborg et al. (1968)
[c]Basal medium as described by Murashige and Skoog (1962)
[d]B-5 vitamin mixture as described by Gamborg et al. (1968)

Tarwi Transformation Method

Agrobacterium Culture Preparation

Overnight *Agrobacterium* cultures in 2YT medium with appropriate antibiotics (30 mg/l rifampicin, 25 mg/l gentamycin; PPS2, 50 mg/l each of rifampicin, gentamycin and spectinomycin), were harvested by brief centrifugation and re-suspended in fresh 2YT media without antibiotics. For co-cultivation, the *Agrobacterium* suspension was diluted to a final OD of 0.06 at A660.

Plant Material and Preparation of Explants

*Lupinus mutabilis* Sweet (tarwi) seeds were obtained from the National Plant Germplasm System of the USDA (Bethesda, Md.). Seeds were sterilized for 1 min in 70% ethanol followed by 20 min in 10% commercial bleach solution (Javex™) equivalent to 1% (w/v) NaOCl. The seeds were rinsed thoroughly with sterile distilled $H_2O$ and imbibed on wet filter paper in deep Petri dishes (100×25-mm) at room temperature (23° C.) in the dark for approximately 18 h (overnight). Fully imbibed seeds with intact seed coats (i.e. radicle not emerged) were used for explant isolation. To isolate the embryo, the seed coat was removed and one cotyledon as well as half of the radicle was excised. The remaining cotyledon with the embryo axis still attached was secured with forceps and the embryo axis was cut into longitudinal sections with a blade that had been dipped into the *Agrobacterium* suspension.

Figure 3:
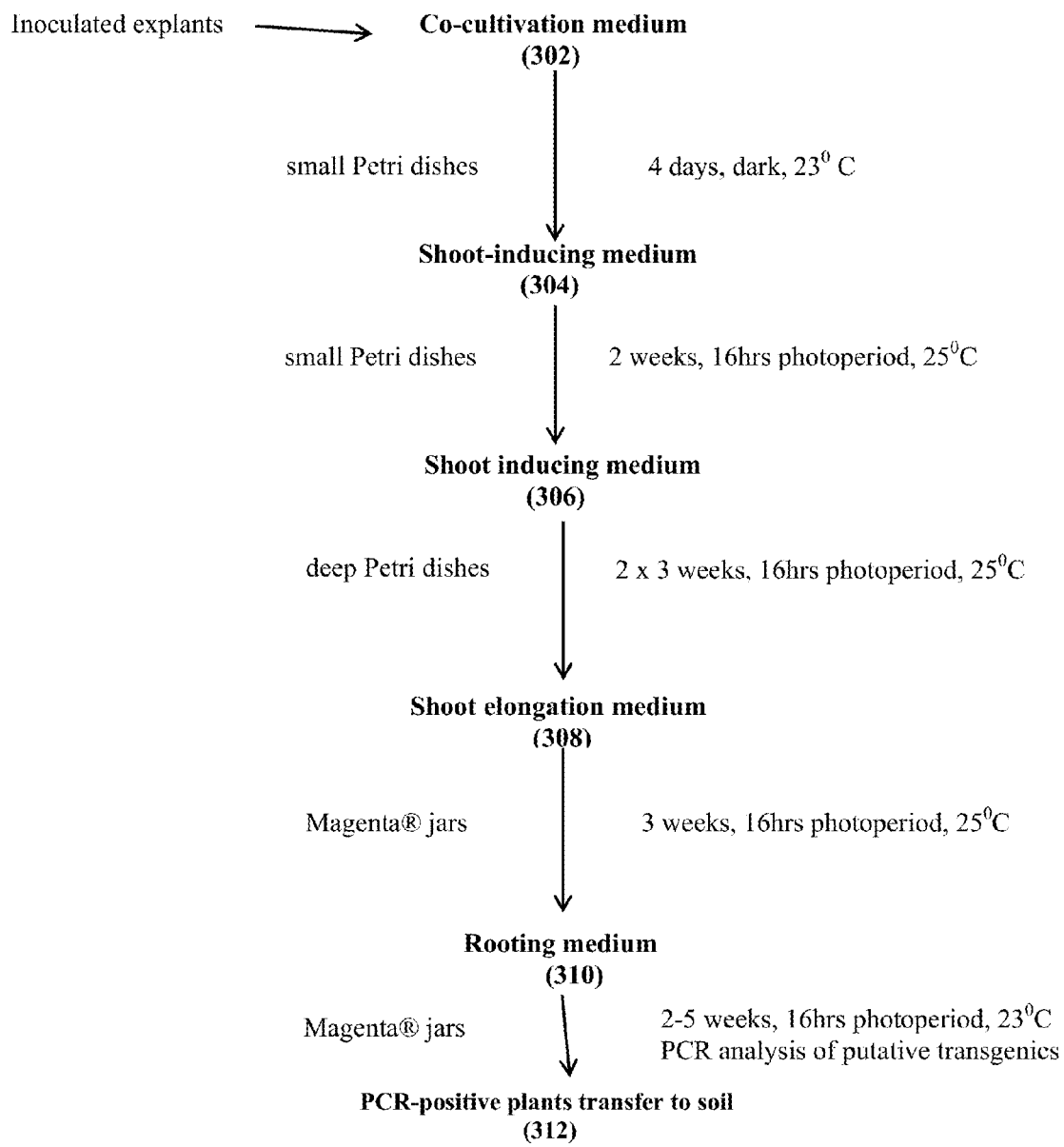
FIG. 3 is a schematic illustrating a method of transforming tarwi.

FIG. 3 is a schematic illustrating the method of tarwi transformation (300).

Timentin® to reduce growth of *Agrobacteria*. Explants were cultivated in small Petri dishes (60×15 mm) for the first 2 weeks of incubation on the shoot initiation medium and then transferred to the same shoot inducing medium but in larger, deep Petri dishes to accommodate the growth of the explants for two additional 3 week cycles (306). The first flush of shoots developing within the first five weeks of cultivation on shoot inducing medium were excised and discarded, as they have been found to arise from pre-existing meristems. The base of the original explant was cut off when it was possible to do so without damaging any developing bud primordia.

One of the factors that affected regeneration and transformation efficiencies of tarwi was severe browning of the media, beginning during incubation on the shoot induction medium. This is a common problem with legume species (Bottinger et al. 2001; Olhoft et al. 2001), and is believed to result from released phenolics and elevated ethylene production. Approaches which can be implemented to eliminate or at least reduce the negative effect of browning include addition of antioxidants, buffering media with MES and adding agents such as silver nitrate to inhibit production of ethylene (Nguyen et al. 2007). An additional approach to reduce browning is to reduce ethylene accumulation by enhancing ventilation. Replacement of Parafilm® for wrapping Petri plates with surgical tape substantially reduced tissue and medium browning and increased the quality and survival rate of explants.

Wild type (control) tarwi explants were screened for their sensitivity to kanamycin to establish concentrations needed to eliminate non-transformed regenerated shoots. It was determined that a minimal concentration of 50 mg/L kanamycin in the shoot-inducing medium was required over at least 5 weeks of cultivation. Higher concentrations of kanamycin (75 and 100 mg/L) killed explants too rapidly before shoot regeneration was initiated.

Shoot Elongation

After 8 weeks on shoot initiation medium, surviving explants had expanded in size and single or multiple shoots were initiated. Clusters of buds were transferred to the shoot elongation medium (308), see Table 2. At each transfer, the clusters of shoots were separated into smaller pieces both to minimize competition and to expose all of the tissue to selection pressure.

Reducing the kanamycin to 25 mg/L in the shoot elongation medium after the initial selection on the higher level of kanamycin minimized non-transformed escapes and maximized the number of transgenic shoots that survived.

The browning which first appeared during the shoot induction phase was more intense and developed more rapidly after explants were transferred to the shoot elongation medium. The substitution of surgical tape for Parafilm® had a pronounced beneficial effect on the number of developing shoots.

In addition to a reduction in the browning of the medium, improvements in ventilation introduced by using MAGENTA™ jars with vented lids also reduced other common problems observed in tissue culture including vitrification, early flowering and poor apical meristem expansion. The enhanced stem development significantly improved the rooting capacity of shoots and the viability of rooted plantlets after transfer to soil.

Rooting

A major hurdle in the development of the tarwi transformation protocol was a low rooting efficiency which is typical of legumes, (Bean et al. 1997; Krishnamurthy et al. 2000, Babaoglu et al. 2000, Polowick et al., 2000, 2004). When individual shoots reached approximately 2 cm in height they were cut off and transferred to rooting medium (310) in MAGENTA™ boxes at a reduced temperature (23° C.), (Chitty et al. 2003). Different medium formulations (full strength and half strength basal salts) plant growth regulators (naphthalene acetic acid, indole butyric acid) as well as structural media (vermiculite, rock wool, agar) were tested. It was determined that an important factor for rooting was the inclusion of freshly prepared IBA.

Transformation procedures for other large-seeded legumes have shown that as high as 70% of surviving shoots to be "escapes", non-transformed shoots/plants that escaped being killed by the selection system (Nadolska-Orczyk and Orczyk 2000). The optimized tarwi transformation procedure results in a low frequency of escapes of only 12.8%.

Transferring of Rooted Plants to the Soil and Growth of Transgenic Tarwi

Roots were visible within 10 days of cultivation on rooting medium and, after 2-3 weeks, rooted plantlets were transferred to soil (312). DNA extracted from leaf material of each rooted plantlet was tested by PCR for the presence hADA and nptII gene sequences and only PCR-positive plants were transferred to soil.

Once shoots were 5-10 cm in length with well-developed roots, the agar was carefully washed off the roots and the small plantlets were transferred to commercial potting soil (Sunshine Mix #4, Sun Gro Horticulture Inc., Bellevue, Wash.) in 10 cm plastic pots.

To maintain the humidity, each plantlet was covered with a clear plastic cup. The pots with plants were arranged in trays which, in turn, were covered with clear plastic domes. Trays were kept in a controlled environment chamber with a 16 h photoperiod and 24/20° C. day/night temperature regime; the plants were watered as required, and fertilized biweekly with 20:20:20 (Plant Products Co., Bramalea, Ontario). The plastic cups were removed after 7-10 days; however, the whole tray remained covered with the plastic dome for a further week until plants had grown to at least 15 cm in height. Plants could be then transplanted to larger pots, if required.

Figure 4:
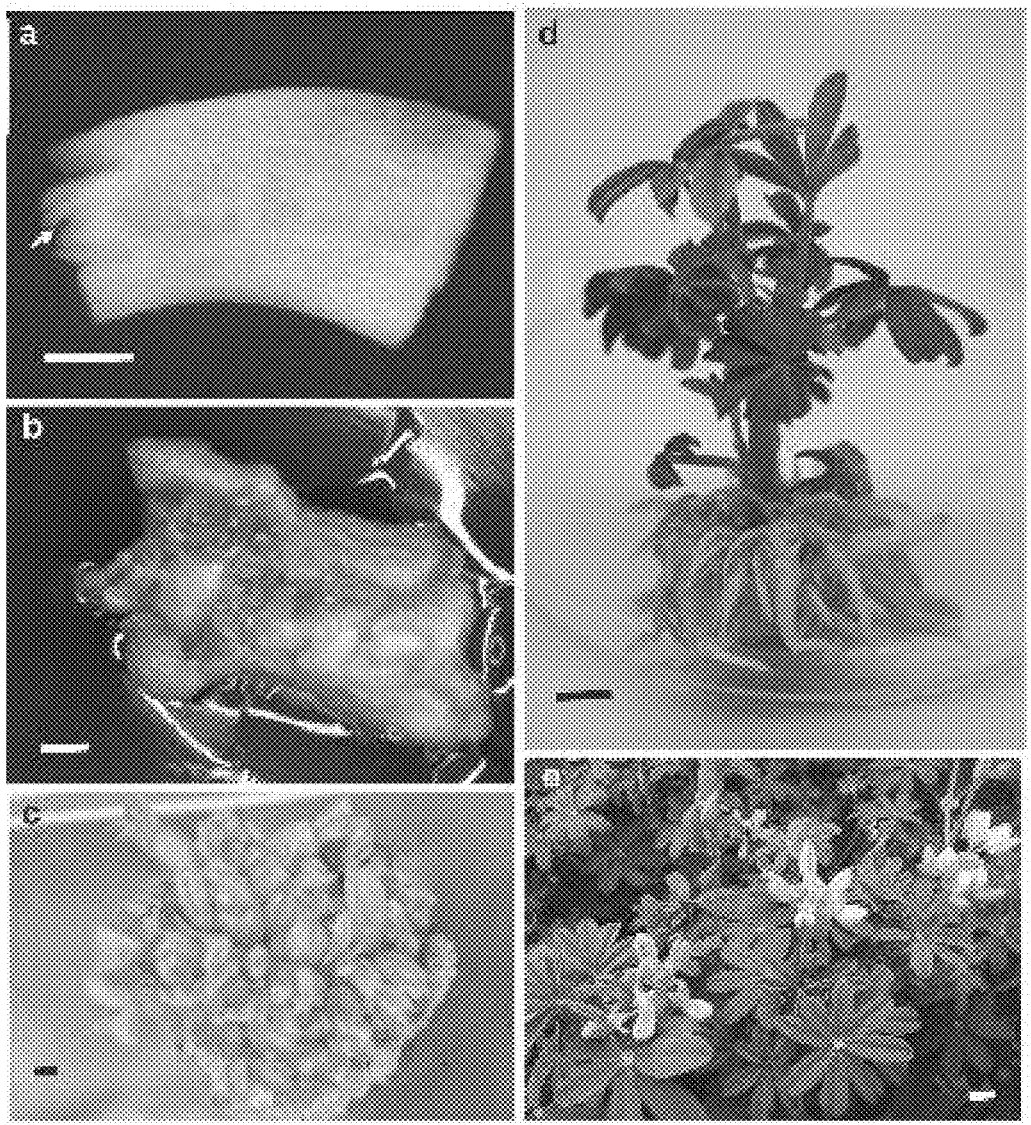
FIG. 4 depicts the stages of tarwi transformation in panels a) to e).

FIG. 4 depicts the stages of tarwi transformation. An embryo explant at the time of co-cultivation is shown in panel a. Longitudinal slices through imbibed mature embryo axes were placed onto sterile filter paper on the surface of the co-cultivation medium. The arrow on the left indicates the shoot meristem. Panel b shows an explant after seven weeks on shoot induction medium with developing shoot meristems in the vicinity of the original meristematic region. After 8 weeks on shoot initiation medium, surviving explants had expanded in size and single or multiple shoots were initiated. Clusters of buds (panel c) were transferred to the shoot elongation medium. Cluster of shoots on an embryo-derived explant after cultivation on shoot elongation (SEM) medium for 6 weeks are shown in FIG. 4 (panel d). Roots were visible within 10 days of cultivation on rooting medium and, after 2-3 weeks, rooted plantlets (FIG. 4, panel d) were transferred to soil. FIG. 4 (panel e) shows a fully fertile transformed tarwi plant. The bar shown in each panel of FIG. 4 represents 1 cm.

Production of Tarwi Plants with Seed Specific Expression of rhADA

ADA Colorimetric Detection Assay

Figure 5:
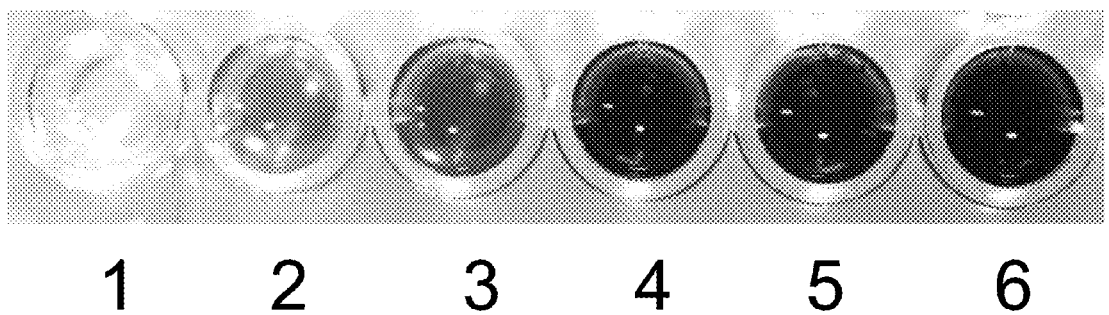
FIG. 5 shows the activity of recombinant hADA in tarwi seed.

FIG. 5 shows the expression and isolation of recombinant hADA in tarwi seed. Five mature T1 seeds from each transgenic tarwi line carrying the hADA gene were chosen randomly. Approximately 25 mg of cotyledon tissues was excised from each seed. Each sample was homogenized with 400 µl of chilled protein extraction buffer (Petolino et al. 2000) and centrifuged at 14,000 rpm for 10 minutes. The supernatant from each sample was used for ADA enzyme colorimetric assay by following the Bio-Quant adenosine deaminase assay kit protocol, (Bio-Quant; Catalogue # BQ 014-EALD) wherein ADA activity eventually manifests as a pink/purple color. The intensity of this color is related to the concentration of active enzyme and can be quantified at 550 nm. Increased staining is indicative of greater ADA activity.

Sample 1 of FIG. 5 shows the lack of ADA activity in the negative control which is wild type tarwi seed. Sample 2 shows the activity of a positive control (ADA from BQ Kit). Sample 3 shows the ADA activity of T1 seeds from transgenic tarwi line TA10. Lane 4 shows the ADA activity of T1 seeds from transgenic tarwi line TA11. Sample 5 shows the activity in T1 seeds from transgenic tarwi line TA12 and sample 6 shows ADA activity in T1 seeds from the transgenic tarwi line TA13.

PCR and Southern Blot Analysis for the Transgene

Plant genomic DNA was extracted from 100 mg of in vitro plant leaf material from each putative transgenic tarwi plants. The CTAB extraction method (Stacey and Isaac, 1994) was followed to extract genomic DNA for PCR screening and Southern blot analysis (Sambrook et al. 1989). The presence of the transgene, hADA was confirmed by PCR amplification using the following specific primer pairs: hADA-fw (5'-GGTGCTTGGAAGCCTGATAC-3') SEQ ID NO:12, and hADA-rv (5'-ACCAGCAGAAGCA-GAAGGAG-3') SEQ ID NO:13.

For Southern blot analysis, 20 μg of genomic DNA from selected T0 transgenic lines of tarwi was digested overnight with HindIII at 37° C. After digestion, all of the digestion reactions were loaded into deep wells of 1% agarose gel and separated by running at 60-65 V for 16-18 h. DNAs were transferred by capillary blotting onto a positively charged nylon membrane (Roche; Catalogue #1-209-299) using the method of Sawada et al. (1995). Digoxigenin-labelled hADA probes were generated by using a PCR DIG probe synthesis kit (Roche; Catalogue #1-636-090). Hybridization and detection of probe was carried out using a non-radioactive, DIG luminescent detection kit for nucleic acids (Roche; 1-363-514) according to the manufacturer's instructions.

Immunoblot Analysis

About 100 mg of T1 seeds from tarwi was homogenized in 400 μl of chilled protein extraction buffer and total protein was isolated according to Petolino et al., (2000). Protein concentration was determined using a standard Bio-Rad Protein Analysis protocol (Bio-Rad; Catalogue #500-006). The extract was diluted to 2 μg/μl of total protein using the extraction buffer. Following a standard procedure for protein separation (Simpson et al., 2009), 50 μg of protein was loaded in each well of a 10% SDS-Polyacrylamide gel for electrophoresis. Subsequently, the protein was transferred onto a PVDF membrane using a trans-blot SD semi-dry electrophoretic transfer cell (Bio-Rad; Catalogue #170-3940). Remaining steps for Immuno blotting were carried out as per the instructions given in HRP color blot starter kit 1 (Bio-Rad; Catalogue #170-5050). The primary antibody used in this experiment was mouse monoclonal antibody raised against amino acids 64-363 of adenosine deaminase of human origin (Santa Cruz Biotechnology, Inc; Cat # SC-18346).

Figure 6:
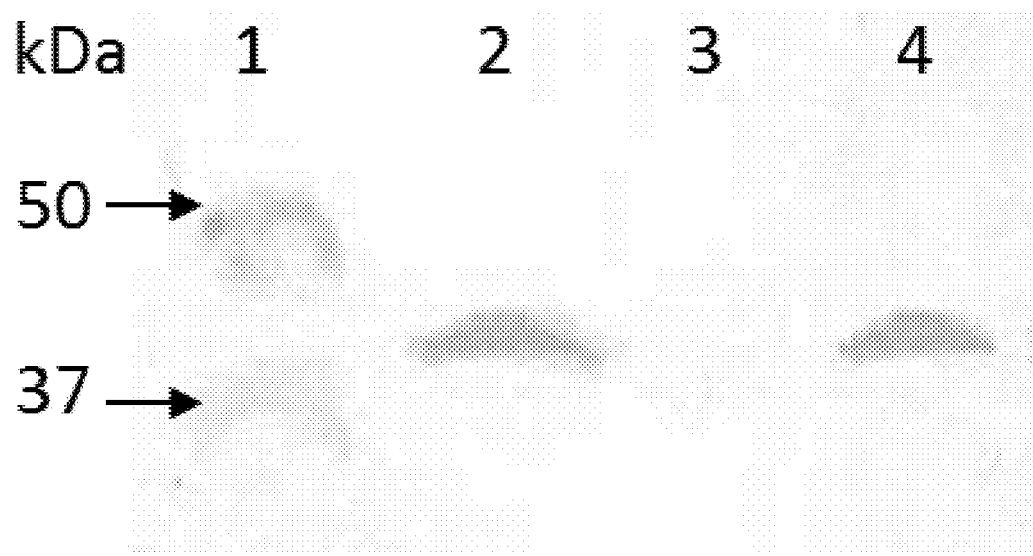
FIG. 6 shows the expression of hADA in tarwi seed.

Western blot analysis of the protein lysate is shown in FIG. 6. Lane 1 shows the Bio-Rad precision plus protein standards. Lane 2 contains extract from transgenic tarwi expressing human ADA. Lane 3 is a negative control which contains extract from non-transgenic tarwi seed (wild type tarwi seed). Lane 4 is a positive control in which recombinant human ADA from Sigma was loaded. The blot was probed with ADA antibody.

EXAMPLE 2

Purification of ADA from Tarwi Seed

Scale-up Production of Transformed Tarwi Seed

Individual primary transformants produced by the method of example 1 were assessed for ADA expression and transgenic gene copy number. Plants with single copy numbers and high levels of expression were selected and selfed to derive homozygous plants. Seed was produced from these plants under confinement as follows: Viable *L. mutabilis* seed is generally cream colored with both sides noticeably convex. Only seeds that appeared viable were planted. Seeds were germinated in 6 cm seed pots that are filled level to the top with the prepared soil mix. A one cm deep indentation was poked into the surface of each pot and one seed placed into the indentation and then lightly covered with soil. Clear plastic covers were placed over the trays to retain humidity and the trays were placed away from direct light sources. On day 3, the outer hull of each seed was manually removed and the soil mounded in the center of each pot to a height of about 2.5 cm. A 1 cm deep indentation was made in the center of the mound and the seed was replanted, root down.

The seed was gently covered with 1 cm of moist soil and the clear covers were replaced. Plants were re-potted when at least one set of true leaves was fully emerged.

Sterilized 10 liter pots for each seedling were filled three quarters full with pasteurized soil. Seedlings were removed from the starter tray and placed in the large pot. Soil was added, lifting the plant as needed, until the soil line was about 2.5 cm below the surface of the 10 liter pot. About 2 g of iron chelate was sprinkled on the soil surface of each pot, near the base of the plants. Pots were attached to an automatic Argus watering system.

The timing and frequency of water delivery (2-3 times per week) was controlled by the Argus System that supplied water as needed until the plants were large enough to require daily watering. Plants were watered four times daily for three minute periods until the plants begin flowering. When the plants begin flowering, the watering time was changed to seven minute periods starting at 7:30 am, 8:30 am, 9:30 am.

A stock solution of plant nutrients was prepared as needed. The nutrients were supplied to the plants, via an inline fertilizer injector, using the water supply system described above.

The following nutrient solution was used to water the plants daily beginning two to four weeks after the date seeds are started and continuing until plants begin to set pods. Four gallons of nutrient solution comprised:

2000 g of 15-15-18 water soluble fertilizer
500 g of MgSO$_4$
100 g of iron chelate The Dosatron fertilizer injector was set to 1:200.

The above procedure delivered nutrients to the plants at the following concentrations:

| | |
|---|---|
| Nitrogen (N) | 100 ppm |
| Phosphorous (P) | 100 ppm |
| Potassium (K) | 120 ppm |
| Magnesium (Mg) | 16 ppm |
| Sulfur (S) | 22 ppm |
| Iron (Fe) | 3 ppm |

Pod Production

The following nutrient solution is used to water the plants daily beginning when the plants started to set pods. Four gallons of nutrient solution comprised:

1200 g of 15-15-18
100 g of iron chelate
250 g of MgSO$_4$

The Dosatron fertilizer injector was set to 1:200.

The above procedure delivered nutrients to the plants at the following concentrations:

| | |
|---|---|
| Nitrogen (N) | 60 ppm |
| Phosphorous (P) | 60 ppm |
| Potassium (K) | 72 ppm |
| Magnesium (Mg) | 8 ppm |
| Sulfur (S) | 11 ppm |
| Iron (Fe) | 3 ppm |

Harvesting:

Mature seed pods are light tan, with no visible green, completely hard and will rattle when shaken. Mature pods were removed from the plant by cutting the stem at the branch point directly below the seed pod. Pods were opened by pressing against the front of the seed pod until it popped open. Seeds were inspected and only those that are smooth, uniformly cream in color, and evenly rounded on both sides were kept.

Seed Storage

Seed was stored in labeled cloth specimen bags at 4 degrees Celsius (40 degrees Fahrenheit).

Aqueous Extraction from the Seed 60 g of the recombinant tarwi seed containing hADA was pulverized thrice for ten seconds at maximum speed in a kitchen-grade electric coffee mill. This flour was transferred to a lab-grade electric blender (Waring model 34BL97) along with 0.40 L of extraction buffer (0.050 M (2-(N-Morpholino)ethanesulphonic acid (MES), in water, pH 6.0 using sodium hydroxide) and mixed at maximum speed for 15 seconds. The blender was rinsed with 0.10 L then 0.050 L of buffer and the pooled fluids were dispensed into the centrifugation bottles, including an additional 0.050 L of buffer bringing the total to 0.60 L of buffer for the 60 g of seed. Solids were removed from this suspension by centrifugation (+5° C., 66 minutes, Beckman JA-14 rotor at 14,000 rpm). To induce precipitation of tarwi proteins, the fluid phase, containing the aqueous fraction and the floating lipid pad, was pooled in a 1 L glass beaker and placed in a +60° C. water bath for 18 minutes, with continuous, gentle stirring. The beaker was then transferred to an ice bath and placed in a refrigerator (+2 to +8° C.) for an hour and then subjected to the same centrifugal conditions. The decanted fluid phase was pooled and refrigerated for 72 hours and then centrifuged again. The decanted fluid was vacuum-filtered twice (Whatman GF/F then Millipore nylon GNEPO4700) to generate the final extract.

Purification by Chromatography

All of the following steps were performed at room temperature (+20 to +25° C.) with overnight storage in the refrigerator (+2 to +8° C.). All solvents were vacuum filtered before use through a 0.20 micron membrane (Millipore nylon GNWPO4700).

The extract was passed at a rate of 23 cm/h through a column of Affi-Gel® Blue Gel (Bio-Rad, 100-200 mesh, d=2.6 cm, l=16 cm) which had been equilibrated with extraction buffer. This was done to reduce tarwi protein, not to bind hADA. The flowthrough was mixed with a solution of ammonium sulfate dissolved in extraction buffer at the weight ratio of 1.0:1.7:6.9 (ammonium sulfate:extraction buffer:Affi-Gel® Blue Gel flowthrough) then vacuum filtered through a 0.20 micron membrane (Millipore nylon GNWPO4700). This filtrate was passed at 300 cm/h through a column of Capto™ Phenyl (high sub) (GE Healthcare, d=1.6 cm, l=16.5 cm) which had been equilibrated with aqueous 1.2 M ammonium sulfate, 0.050 M MES, pH 6.0, using sodium hydroxide. This was done to bind the hADA which was then eluted by a 16.5 minute linear gradient vs extraction buffer. The elution was divided into 14.5 mL fractions and fractions containing hADA activity at the desired purity were pooled. This pool was divided into 13 mL aliquots and each was passed at 113 cm/h through a HiPrep™ 26/10 Desalting column (GE Healthcare, d=2.6 cm, I=10.0 cm) which had been equilibrated with aqueous 0.050 M Tris-(hydroxymethyl)aminomethane (Tris), pH 7.0 with hydrochloric acid (HCl). This was done as a buffer exchange step. The pool from these desalting cycles was diluted 2.5-fold with water and passed at 300 cm/h through a column of BioRad Macro-Prep DEAE (d=1.6 cm, l=13.5 cm) which had been equilibrated with aqueous 0.020 M Tris-HCl, pH 7.0. This was done to bind the hADA which was then eluted at 150 cm/h by a 27 minute linear gradient vs 0.050 M Tris-HCl, pH 7.0, 0.20 M potassium chloride. The elution was divided into 14.5 mL fractions and fractions containing hADA activity at the desired purity were pooled. The pooled fractions from the DEAE step were diluted with 0.050 M Tris-HCl, pH 7.0 and glycerol to give a final concentration of 1 U/mL (+25° C.) and 20% v/v glycerol and stored at −15 to −25° C.

The above-described embodiments are intended to be examples only. Alterations, modifications and variations can be effected to the particular embodiments by those of skill in the art without departing from the scope, which is defined solely by the claims appended hereto.

REFERENCES

All documents listed herein are incorporated by reference, including the following documents for which a full citation is provided below.

Asad, S., et al., (2008) Silicon carbide whisker-mediated embryonic callus transformation of cotton, (*gossypium hirsutum* L.) and regeneration of salt tolerant plants, Mol. Biotechnol. 40(2): 161-9.

Ausubel et al., Current Protocols in Molecular Biology, John Wiley & Sons, New York, N.Y., 1998, Babaoglu M, McCabe M, Power J, Davey M (2000) *Agrobacterium*-mediated transformation of *Lupinus mutabilis* L. using shoot apical explants. Acta Physiol Plant 22:111-119

Bean S J, Gooding P S, Mullineaux P M, Davies D R (1997) A simple system for pea transformation. Plant Cell Rep 16:513-519

Böttinger P, Steinmetz A, Schieder O, Pickardt T (2001) *Agrobacterium*-mediated transformation of *Vicia faba*. Mol Breed 8:243-254

Chitty J A, Allen R S, first A J, Larkin P J (2003) Genetic transformation in commercial Tasmanian cultivars of opium poppy, *Papaver somniferum*, and movement of transgenic pollen in the field. Functional Plant Biol 30:1045-1058

Daddona, et al., “Human Adenosine Deaminase, cDNA and complete primary amino acid sequence” The Journal of Biological Chemistry, vol 259, No 19, October 10, pp 12821-12106, 1984)

Ellis, et al., (1988), Tissue specific expression of a pea legumin gene in seeds of Nicotiniana plumbaginifolia, Plant Molec. Biol 10:203-214.

Fischer, R., et al., (2004), Plant-based production of biopharmaceuticals, Current Opinions in Plant Biology 7:152-158

Gamborg O L, Miller R A, Ojima K (1968) Nutrient requirements of suspension cultures of Nutrient requirement suspension cultures of soybean root cells. Exp Cell Res 50: 151-158.

Gelvin, S. B., (2003), *Agrobacterium*-mediated plant transformation: the biology behind the “gene-jockeying” tool. Microbiology and Molecular Biology Reviews, pp 16-37.

Gusti G, and Galanti, B. (1984). Methods of Enzymatic Analysis. Vol. IV (pp. 315-323).

Hills, M., et al., (2007), “Genetic use restriction technologies [GURTS]: strategies to impede transgene movement”, Trends in Plant Science 12(4): 177-183).

Jaiswal, R., et al., (2007), Isolation of pigeon pea (*Cajanus cajan* L.,) legumin gene promoter and identification of conserved regulatory elements using tools of bioinformatics. Indian J of Biotechnology Vol 6: 495-503.

Jefferson, R. A. (1987). Assaying chimeric genes in plants: The GUS gene fusion system. Plant MOl. Biol. Rep. 5: 387-405.

Karimi, M., De Meyer, B. and Hilson, P. (2005) Modular cloning and expression of tagged fluorescent protein in plant cells. Trends Plant Sci., 10, 103-105.

Koncz, C. and Schell, J. (1986) The promoter of the TL-DNA gene 5 controls the tissue-specific expression of chimeric genes carried by a novel type of *Agrobacterium* binary vector. Mol. Gen. Genet., 204, 383-396.

Li H, Wylie S J, Jones M G K (2000) Transgenic yellow lupin (*Lupinus luteus*). Plant Cell Rep 19:634-637

Liu, Y. J., Yuan, Y., Zheng, J., Tao, Y. Z., Dong, Z. G., Wang, J. H. and Wang, G. Y. (2004) Signal Peptide of Potato PinII Enhances the Expression of Cry1Ac in Transgenic Tobacco. Acta Biochimica et Biophysica Sinica, 36: 553-558.

Lycett Q. W., et al., (1985), "The 5' flanking regions of three pea legumin genes: Comparison of the DNA sequences, Nucleic Acid Research 13:6733-6743".

Maliga, P., (2004), Plastid transformation in higher plants, Annu. Rev. Plant Biol 55:289-313.

Maniatis et al., in Molecular Cloning (A Laboratory Manual), Cold Spring Harbor Laboratory, (1982) p 387 to 389.

Martinez-Navio et al., (2011) "An old enzyme for current needs: adenosine deaminase and a dendrytic vaccine for HIV, Immunology and Cell Biology, 20 September, doi: 10.1038/icp.2011.8

Molvig L, Tabe L M, Eggum B O, Moore A E, Craig S, Spencer D, Higgins T J V (1997) Enhanced methionine levels and increased nutritive value of seeds of transgenic lupins (*Lupinus angustifolius* L.) expressing a sunflower seed albumin gene. Proc Natl Acad Sci USA 94:8393-8398

Mulin M, Bellio-Spataru A (2000) Organogenesis from hypocotyl thin cell layers of *Lupinus mutabilis* and *Lupinus albus*. J Plant Growth Regul 30:177-183

Murashige T, Skoog F (1962) A revised medium for rapid growth and bioassays with tobacco tissue cultures. Physiol Plant 15:473-497

Nadolska-Orczyk A (1992) Somatic embryogenesis of agriculturally important lupin species (*Lupinus angustifolius, L. albus, L. mutabilis*). Plant Cell Tissue Organ Cult 28:19-25.

Nadolska-Orczyk A, Orczyk W (2000) Study of the factors influencing *Agrobacterium*-mediated transformation of pea (*Pisum sativum* L.). Mol Breed 6:185-194

Nguyen T V, Thanh Thu T, Claeys M, Angenon G (2007) *Agrobacterium*-mediated transformation of sorghum (*Sorghum bicolor* (L.) Moench) using an improved in vitro regeneration system. Plant Cell Tissue Organ Cult 91:155-164

Olhoft P, Lin K, Galbraith J, Nielsen N, Somers D (2001) The role of thiol compounds in increasing *Agrobacterium*-mediated transformation of soybean cotyledonary-node cells. Plant Cell Rep 20:731-737

Petolino J. F., Young, S., Hopkins, N., Sukhapinda, K., Woolsey, A., Hayes, C., and Pelcher, L. (2000), Expression of murine adenosine deaminase (ADA) in transgenic mice. Transgenic Research 9: 1-9.

Pigeaire A, Abernethy D, Smith P M, Simpson K, Fletcher N, Lu C Y, Atkins C A, Cornish E (1997) Transformation of a grain legume (Lupinus angustifolius L.) via *Agrobacterium tumefaciens*-mediated gene transfer to shoot apices. Mol Breed 3:341-349

Pniewski T, Kapusta J, Legocki A (2002) In vitro micropropagation of four lupin species. Acta Physiol Plant 24:417-424

Polowick P L, Baliski D S, Mahon J D (2004) *Agrobacterium tumefaciens*-mediated transformation of chickpea (*Cicer arietinum* L.): Gene integration, expression and inheritance. Plant Cell Rep 23:485-491.

Polowick P L, Quandt J, Mahon J (2000) The ability of pea transformation technology to transfer genes into peas adapted to western Canadian growing conditions. Plant Sci 153:161-170.

Rerie W. G., Whitecross, M. I., and Higgins, T. J. V. (1991) Nucleotide sequence of an A-type legumin gene from pea. Nuc. Acids. Res. 18: 655.

Schernthaner, J. P., et al., (2003), A repressible system to prevent seed germination—Implications for controlling transgenes under agricultural conditions, PNAS 100(11) 6855-6859.

Sharma, A. K., et al., (2009), Plants as bioreactors: recent developments and emerging opportunities, Biotechnology Advances 27:811-832.Singhabahu, S., Bringloe, D., and George, J. (2010), Expression of a functional human adenosine deaminase in tobacco plant cell suspensions and whole plants, Conference Proceedings from Recombinant pharmaceutical manufacturing from plants—the future of molecular farming.

Singhabahu, S, and Bringloe D. (2012) Production of human adenosine deaminase in tobacco BY2 calli and cell suspensions, Conference Proceedings from Molecular Pharming—recent progress in manufacturing medicines in plants.

Spok et al., (2008) Plant Molecular Farming; Opportunities and Challenges. J R C, European Commission, EUR 23383, DOI 10.2791/30861

Ward, W., et al., (2009), Protein purification, Current Analytical Chemistry 5(2):1-21.

Ziolkowski, M. J., (2007) Advancements in biolistics and applications for agriculturally significant crops, MMG445 Basic Biotechnology e Journal 3:34-39.

---

What is claimed is:

1. A method of producing transformed tarwi comprising a human adenosine deaminase (hADA) or a functional variant thereof, the method comprising:
   slicing at least one tarwi seed embryo to produce at least one explant comprising mature tarwi seed embryo tissue, wherein said slicing comprises longitudinally slicing the embryo;
   infecting the explant with *Agrobacterium* and incubating in a co-cultivation medium comprising acetosyringone, and being free of auxins and cytokinins; wherein the *Agrobacterium* comprises a polynucleotide sequence encoding the human adenosine deaminase (hADA) or functional variant thereof; thereby generating a transformed explant;
   inducing at least one transformed shoot by incubating the transformed explant in a shoot induction medium comprising 6-benzylaminopurine, kanamycin and timentin;
   elongating the at least one transformed shoot to form an elongated shoot, comprising incubating the transformed shoot in a shoot elongation medium in a ventilated jar, said elongation medium comprising 6-benzylaminopurine, kanamycin, and timentin;
   rooting said elongated shoot in a rooting medium comprising indole-3-butyric acid (IBA), kanamycin, and timentin; and
   regenerating a transformed tarwi plant from the elongated shoot after rooting for 2-3 weeks.

2. The method of claim 1, wherein infecting the explant with *Agrobacterium* comprises slicing the tarwi seed embryo longitudinally using a scalpel having the *Agrobacterium* thereon.

3. The method of claim 1, wherein the co-cultivation medium comprises Gamborg B5 salts.

4. The method of claim 1 further comprising removing the elongated shoot from the transformed explant prior to regenerating.

5. The method of claim 1, wherein the hADA comprises the amino acid sequence of SEQ ID NO:1.

6. The method of claim 1, wherein the functional variant of hADA comprises an amino acid sequence that is at least 80% identical to the amino acid sequence of SEQ ID NO:1, and the functional variant is capable of deaminating adenosine.

7. The method of claim 1, wherein the functional variant of hADA comprises the amino acid sequence as set forth in SEQ ID NO:2.

8. The method of claim 1, wherein the polynucleotide sequence is as set forth in SEQ ID NO:3, SEQ ID NO:4, or SEQ ID NO:5; or is a polynucleotide sequence with 80% or greater identity to SEQ ID NO:3, SEQ ID NO:4, or SEQ ID NO:5.

9. The method of claim 8, wherein the polynucleotide sequence has 85% or greater identity to SEQ ID NO:3, SEQ ID NO:4, or SEQ ID NO:5.

10. A transformed tarwi plant produced by the method of claim 1.

11. A transformed seed of the plant of claim 10.

12. A transformed cell of the seed of claim 11.

13. The method of producing transformed tarwi according to claim 1, wherein the co-cultivation medium comprises Gamborg B5 salts, vitamins, sucrose, 200 μM acetosyringone and agar, at pH 5.75.

14. The method of producing transformed tarwi according to claim 1, wherein the shoot induction medium comprises Gamborg B5 salts, vitamins, 13 µM 6-benzylaminopurine, sucrose, kanamycin, and agar, at pH 5.75.

15. The method of producing transformed tarwi according to claim 1, wherein the shoot elongation medium comprises salts, vitamins, about 0.5 µM 6-benzylaminopurine, sucrose, kanamycin, timentin and agar, at about pH 5.75.

16. The method of producing transformed tarwi according to claim 1, wherein the rooting medium comprises Gamborg B5 salts, vitamins, sucrose, about 20 µM indole-3-butyric acid (IBA), kanamycin, timentin and agar, at about pH 5.6.

* * * * *

SEQUENCE LISTING

```
<160> NUMBER OF SEQ ID NOS: 13

<210> SEQ ID NO 1
<211> LENGTH: 363
<212> TYPE: PRT
<213> ORGANISM: Homo sapiens

<400> SEQUENCE: 1

Met Ala Gln Thr Pro Ala Phe Asp Lys Pro Lys Val Glu Leu His Val
1               5                   10                  15

His Leu Asp Gly Ser Ile Lys Pro Glu Thr Ile Leu Tyr Tyr Gly Arg
            20                  25                  30

Arg Arg Gly Ile Ala Leu Pro Ala Asn Thr Ala Glu Gly Leu Leu Asn
```

```
            35                  40                  45
Val Ile Gly Met Asp Lys Pro Leu Thr Leu Pro Asp Phe Leu Ala Lys
         50                  55                  60

Phe Asp Tyr Tyr Met Pro Ala Ile Ala Gly Cys Arg Glu Ala Ile Lys
 65                  70                  75                  80

Arg Ile Ala Tyr Glu Phe Val Glu Met Lys Ala Lys Glu Gly Val Val
                 85                  90                  95

Tyr Val Glu Val Arg Tyr Ser Pro His Leu Leu Ala Asn Ser Lys Val
            100                 105                 110

Glu Pro Ile Pro Trp Asn Gln Ala Glu Gly Asp Leu Thr Pro Asp Glu
        115                 120                 125

Val Val Ala Leu Val Gly Gln Gly Leu Gln Glu Gly Glu Arg Asp Phe
    130                 135                 140

Gly Val Lys Ala Arg Ser Ile Leu Cys Cys Met Arg His Gln Pro Asn
145                 150                 155                 160

Trp Ser Pro Lys Val Val Glu Leu Cys Lys Lys Tyr Gln Gln Gln Thr
                165                 170                 175

Val Val Ala Ile Asp Leu Ala Gly Asp Glu Thr Ile Pro Gly Ser Ser
            180                 185                 190

Leu Leu Pro Gly His Val Gln Ala Tyr Gln Glu Ala Val Lys Ser Gly
        195                 200                 205

Ile His Arg Thr Val His Ala Gly Glu Val Gly Ser Ala Glu Val Val
    210                 215                 220

Lys Glu Ala Val Asp Ile Leu Lys Thr Glu Arg Leu Gly His Gly Tyr
225                 230                 235                 240

His Thr Leu Glu Asp Gln Ala Leu Tyr Asn Arg Leu Arg Gln Glu Asn
                245                 250                 255

Met His Phe Glu Ile Cys Pro Trp Ser Ser Tyr Leu Thr Gly Ala Trp
            260                 265                 270

Lys Pro Asp Thr Glu His Ala Val Ile Arg Leu Lys Asn Asp Gln Ala
        275                 280                 285

Asn Tyr Ser Leu Asn Thr Asp Asp Pro Leu Ile Phe Lys Ser Thr Leu
    290                 295                 300

Asp Thr Asp Tyr Gln Met Thr Lys Arg Asp Met Gly Phe Thr Glu Glu
305                 310                 315                 320

Glu Phe Lys Arg Leu Asn Ile Asn Ala Ala Lys Ser Ser Phe Leu Pro
                325                 330                 335

Glu Asp Glu Lys Arg Glu Leu Leu Asp Leu Leu Tyr Lys Ala Tyr Gly
            340                 345                 350

Met Pro Pro Ser Ala Ser Ala Gly Gln Asn Leu
        355                 360

<210> SEQ ID NO 2
<211> LENGTH: 363
<212> TYPE: PRT
<213> ORGANISM: Homo sapiens

<400> SEQUENCE: 2

Met Ala Gln Thr Pro Ala Phe Asp Lys Pro Lys Val Glu Leu His Val
 1               5                  10                  15

His Leu Asp Gly Ser Ile Lys Pro Glu Thr Ile Leu Tyr Tyr Gly Arg
            20                  25                  30

Arg Arg Gly Ile Ala Leu Pro Ala Asn Thr Ala Glu Gly Leu Leu Asn
        35                  40                  45
```

Val Ile Gly Met Asp Lys Pro Leu Thr Leu Pro Asp Phe Leu Ala Lys
 50                  55                  60

Phe Asp Tyr Tyr Met Pro Ala Ile Ala Gly Ser Arg Glu Ala Ile Lys
 65                  70                  75                  80

Arg Ile Ala Tyr Glu Phe Val Glu Met Lys Ala Lys Glu Gly Val Val
                 85                  90                  95

Tyr Val Glu Val Arg Tyr Ser Pro His Leu Leu Ala Asn Ser Lys Val
            100                 105                 110

Glu Pro Ile Pro Trp Asn Gln Ala Glu Gly Asp Leu Thr Pro Asp Glu
        115                 120                 125

Val Val Ala Leu Val Gly Gln Gly Leu Gln Glu Gly Glu Arg Asp Phe
130                 135                 140

Gly Val Lys Ala Arg Ser Ile Leu Cys Cys Met Arg His Gln Pro Asn
145                 150                 155                 160

Trp Ser Pro Lys Val Val Glu Leu Cys Lys Lys Tyr Gln Gln Gln Thr
                165                 170                 175

Val Val Ala Ile Asp Leu Ala Gly Asp Glu Thr Ile Pro Gly Ser Ser
            180                 185                 190

Leu Leu Pro Gly His Val Gln Ala Tyr Gln Glu Ala Val Lys Ser Gly
        195                 200                 205

Ile His Arg Thr Val His Ala Gly Glu Val Gly Ser Ala Glu Val Val
210                 215                 220

Lys Glu Ala Val Asp Ile Leu Lys Thr Glu Arg Leu Gly His Gly Tyr
225                 230                 235                 240

His Thr Leu Glu Asp Gln Ala Leu Tyr Asn Arg Leu Arg Gln Glu Asn
                245                 250                 255

Met His Phe Glu Ile Cys Pro Trp Ser Ser Tyr Leu Thr Gly Ala Trp
            260                 265                 270

Lys Pro Asp Thr Glu His Ala Val Ile Arg Leu Lys Asn Asp Gln Ala
        275                 280                 285

Asn Tyr Ser Leu Asn Thr Asp Asp Pro Leu Ile Phe Lys Ser Thr Leu
290                 295                 300

Asp Thr Asp Tyr Gln Met Thr Lys Arg Asp Met Gly Phe Thr Glu Glu
305                 310                 315                 320

Glu Phe Lys Arg Leu Asn Ile Asn Ala Ala Lys Ser Ser Phe Leu Pro
                325                 330                 335

Glu Asp Glu Lys Arg Glu Leu Leu Asp Leu Leu Tyr Lys Ala Tyr Gly
            340                 345                 350

Met Pro Pro Ser Ala Ser Ala Gly Gln Asn Leu
        355                 360

<210> SEQ ID NO 3
<211> LENGTH: 1092
<212> TYPE: DNA
<213> ORGANISM: Homo sapiens

<400> SEQUENCE: 3
atggcccaga cgcccgcctt cgacaagccc aaagtagaac tgcatgtcca cctagacgga     60
tccatcaagc tgaaaccat cttatactat ggcaggagga gagggatcgc cctcccagct    120
aacacagcag aggggctgct gaacgtcatt ggcatggaca agccgctcac ccttccagac    180
ttcctggcca gtttgactac tacatgcct gctatcgcgg gctgccggga ggctatcaaa    240
aggatcgcct atgagtttgt agagatgaag gccaaagagg gcgtggtgta tgtggaggtg    300
cggtacagtc cgcacctgct ggccaactcc aaagtggagc caatcccctg gaaccaggct    360

```
gaaggggacc tcaccccaga cgaggtggtg gccctagtgg gccagggcct gcaggagggg      420
gagcgagact tcgggtcaa ggcccggtcc atcctgtgct gcatgcgcca ccagcccaac       480
tggtccccca aggtggtgga gctgtgtaag aagtaccagc agcagaccgt ggtggccatt      540
gacctggctg gagatgagac catcccagga agcagcctct tgcctggaca tgtccaggcc      600
taccaggagg ctgtgaagag cggcattcac cgtactgtcc acgccgggga ggtgggctcg      660
gccgaagtag taaaagaggc tgtggacata ctcaagacag agcggctggg acacggctac      720
cacaccctgg aagaccaggc cctttataac aggctgcggc aggaaaacat gcacttcgag      780 atctgccccct ggtccagcta cctcactggt gcctggaagc cggacacgga gcatgcagtc     840
attcggctca aaaatgacca ggctaactac tcgctcaaca cagatgaccc gctcatcttc      900
aagtccaccc tggacactga ttaccagatg accaaacggg acatgggctt tactgaagag      960
gagtttaaaa ggctgaacat caatgcggcc aaatctagtt tcctcccaga agatgaaaag     1020
agggagcttc tcgacctgct ctataaagcc tatgggatgc caccttcagc ctctgcaggg     1080
cagaacctct ga                                                        1092

<210> SEQ ID NO 4
<211> LENGTH: 1092
<212> TYPE: DNA
<213> ORGANISM: Homo sapiens

<400> SEQUENCE: 4
atggctcaaa ctcctgcttt tgataagcct aaggttgaac ttcatgttca tcttgatggt       60
tctattaagc ctgaaactat tctttattat ggtagaagaa gaggtattgc tcttcctgct      120
aatactgctg aaggtcttct taatgttatt ggtatggata agcctcttac tcttcctgat      180
tttcttgcta agtttgatta ttatatgcct gctattgctg ttgtagaga agctattaag       240 agaattgctt atgaatttgt tgagatgaag gctaaggaag gtgttgttta tgttgaagtt      300
agatattctc ctcatcttct tgctaattct aaggttgaac ctattccttg gaaccaagct      360
gaaggtgatc ttactcctga tgaagttgtt gctcttgttg gtcaaggtct tcaagaaggt      420
gaaagagatt ttggtgttaa ggctagatct attctttgtt gtatgagaca tcaacctaat      480
tggtctccta aggttgttga attgtgtaag aagtatcaac agcaaactgt tgttgctatt      540
gatcttgctg gtgatgaaac tattcctggt tcttctcttc ttcctggtca tgttcaagct      600
tatcaagaag ctgttaagtc tggtattcat agaactgttc atgctggtga agttggttct      660
gctgaagttg ttaaggaagc tgttgatatt cttaagactg aaagacttgg tcatggttat      720
catactcttg aagatcaagc tctttataac agacttagac aagagaatat gcattttgaa      780
atttgtcctt ggtcttctta tcttactggt gcttggaagc ctgatactga acatgctgtt      840
attagactta agaatgatca agctaattat tctcttaata ctgatgatcc tcttattttt      900
aagtctactc ttgatactga ttatcaaatg actaagagag atatgggttt tactgaagaa      960
gagtttaaga acttaatat taatgctgct aagtcttctt ttcttcctga agatgaaaag     1020
agagaacttc ttgatcttct ttataaggct tatggtatgc ctccttctgc ttctgctggt     1080
caaaatcttt aa                                                        1092

<210> SEQ ID NO 5
<211> LENGTH: 1092
<212> TYPE: DNA
<213> ORGANISM: Homo sapiens
```

<400> SEQUENCE: 5

```
atggctcaaa ctcctgcttt tgataagcct aaggttgaac ttcatgttca tcttgatggt      60
tctattaagc ctgaaactat tctttattat ggtagaagaa gaggtattgc tcttcctgct     120
aatactgctg aaggtcttct taatgttatt ggtatggata agcctcttac tcttcctgat     180
tttcttgcta agtttgatta ttatatgcct gctattgctg ttctagagaa agctattaag     240
agaattgctt atgaatttgt tgagatgaag gctaaggaag gtgttgttta tgttgaagtt     300
agatattctc ctcatcttct tgctaattct aaggttgaac ctattccttg aaccaagct      360
gaaggtgatc ttactcctga tgaagttgtt gctcttgttg gtcaaggtct tcaagaaggt     420
gaaagagatt ttggtgttaa ggctagatct attctttgtt gtatgagaca tcaacctaat     480
tggtctccta aggttgttga attgtgtaag aagtatcaac agcaaactgt tgttgctatt     540
gatcttgctg gtgatgaaac tattcctggt tcttctcttc ttcctggtca tgttcaagct     600
tatcaagaag ctgttaagtc tggtattcat agaactgttc atgctggtga agttggttct     660
gctgaagttg ttaaggaagc tgttgatatt cttaagactg aaagacttgg tcatggttat     720
catactcttg aagatcaagc tctttataac agacttagac aagagaatat gcattttgaa     780
atttgtcctt ggtcttctta tcttactggt gcttggaagc tgatactga acatgctgtt     840
attagactta agaatgatca agctaattat tctcttaata ctgatgatcc tcttattttt     900
aagtctactc ttgatactga ttatcaaatg actaagagag atatgggttt tactgaagaa     960
gagtttaaga gacttaatat taatgctgct aagtcttctt ttcttcctga agatgaaaag    1020
agagaacttc ttgatcttct ttataaggct tatggtatgc tccttctgc ttctgctggt     1080
caaaatcttt aa                                                        1092
```

<210> SEQ ID NO 6
<211> LENGTH: 54
<212> TYPE: DNA
<213> ORGANISM: Pisum sativum

<400> SEQUENCE: 6

```
ggggacaact ttgtatagaa aagttgaatt ccttcttaat ggtagtctag ttta            54
```

<210> SEQ ID NO 7
<211> LENGTH: 53
<212> TYPE: DNA
<213> ORGANISM: Pisum sativum

<400> SEQUENCE: 7

```
ggggactgct tttttgtaca aacttgtggt tggatagaat atatgtttgt gac             53
```

<210> SEQ ID NO 8
<211> LENGTH: 53
<212> TYPE: DNA
<213> ORGANISM: Solanum tuberosum

<400> SEQUENCE: 8

```
ggggacaagt ttgtacaaaa aagcaggcta ttcacagaca ctcttcaccc caa             53
```

<210> SEQ ID NO 9
<211> LENGTH: 54
<212> TYPE: DNA
<213> ORGANISM: Solanum tuberosum

<400> SEQUENCE: 9

```
ggggaccact ttgtacaaga aagctgggta agccttcgca tcaacatgct ccat            54
```

```
<210> SEQ ID NO 10
<211> LENGTH: 58
<212> TYPE: DNA
<213> ORGANISM: Homo sapiens

<400> SEQUENCE: 10
ggggacagct ttcttgtaca aagtggtgcc tagaatggct caaactcctg cttttgat        58

<210> SEQ ID NO 11
<211> LENGTH: 53
<212> TYPE: DNA
<213> ORGANISM: Homo sapiens

<400> SEQUENCE: 11
ggggaccact ttgtacaaga aagctgggtt tattaaagat tttgaccagc aga             53

<210> SEQ ID NO 12
<211> LENGTH: 20
<212> TYPE: DNA
<213> ORGANISM: Homo sapiens

<400> SEQUENCE: 12
ggtgcttgga agcctgatac                                                  20

<210> SEQ ID NO 13
<211> LENGTH: 20
<212> TYPE: DNA
<213> ORGANISM: Homo sapiens

<400> SEQUENCE: 13
accagcagaa gcagaaggag                                                  20
```